(12) United States Patent
Kermani et al.

(10) Patent No.: US 8,880,456 B2
(45) Date of Patent: Nov. 4, 2014

(54) ANALYZING GENOME SEQUENCING INFORMATION TO DETERMINE LIKELIHOOD OF CO-SEGREGATING ALLELES ON HAPLOTYPES

(75) Inventors: Bahram Ghaffarzadeh Kermani, Los Altos, CA (US); Radoje Drmanac, Los Altos Hills, CA (US)

(73) Assignee: Complete Genomics, Inc., Mountain View, CA (US)

( * ) Notice: Subject to any disclaimer, the term of this patent is extended or adjusted under 35 U.S.C. 154(b) by 241 days.

(21) Appl. No.: 13/591,741

(22) Filed: Aug. 22, 2012

(65) Prior Publication Data
US 2013/0054508 A1 Feb. 28, 2013

Related U.S. Application Data

(60) Provisional application No. 61/527,428, filed on Aug. 25, 2011.

(51) Int. Cl.
| | | |
|---|---|---|
| *G06F 9/44* | (2006.01) | |
| *G06N 7/02* | (2006.01) | |
| *G06N 7/08* | (2006.01) | |
| *G06F 19/18* | (2011.01) | |
| *G06F 19/22* | (2011.01) | |

(52) U.S. Cl.
CPC .............. *G06F 19/18* (2013.01); *G06F 19/22* (2013.01)
USPC .......................................................... 706/52

(58) Field of Classification Search
CPC combination set(s) only.
See application file for complete search history.

(56) References Cited

U.S. PATENT DOCUMENTS

| | | | | |
|---|---|---|---|---|
| 8,133,719 | B2 * | 3/2012 | Drmanac et al. | 435/287.2 |
| 8,298,768 | B2 * | 10/2012 | Drmanac et al. | 435/6.12 |
| 8,407,554 | B2 * | 3/2013 | Kermani et al. | 714/752 |
| 8,415,099 | B2 * | 4/2013 | Drmanac et al. | 435/6.1 |
| 8,440,397 | B2 * | 5/2013 | Drmanac et al. | 435/6.1 |
| 8,445,197 | B2 * | 5/2013 | Drmanac et al. | 435/6.1 |
| 8,518,640 | B2 * | 8/2013 | Drmanac et al. | 435/6.1 |
| 8,551,702 | B2 * | 10/2013 | Drmanac et al. | 435/6.11 |

(Continued)

FOREIGN PATENT DOCUMENTS

WO 2011/038155 A2 3/2011

OTHER PUBLICATIONS

Suk, E., et al., "A Comprehensively Molecular Haplotype-Resolved Genome of a European Individual," Genome Res., published [online] Aug. 3, 2011, [retrieved on Aug. 24, 2011], retrieved from URL: genome.cshlp.org, 45 pages.

(Continued)

*Primary Examiner* — Michael B Holmes
(74) *Attorney, Agent, or Firm* — Kilpatrick Townsend & Stockton LLP; David B. Raczkowski

(57) ABSTRACT

Sequencing information is used to correlate alleles at certain locations to alleles at other locations. The statistical information from the reads of fragments in a sample can be used to determine the phasing of haplotypes and to correct or confirm based calls at the locations. In one example, a confidence value (strength score) is determined for a particular hypothesis, which can include whether two alleles are on a same haplotype at two particular loci, as well as what the alleles are on another haplotype (e.g. for a diploid organism). The strength can include a positive contribution from data that is consistent with the hypothesis and a negative contribution from data is that inconsistent with the hypothesis, where both values can be used in a formula to determine the strength.

26 Claims, 25 Drawing Sheets

(56) References Cited

U.S. PATENT DOCUMENTS

| | | | | |
|---|---|---|---|---|
| 8,592,150 | B2* | 11/2013 | Drmanac et al. | 435/6.1 |
| 8,609,335 | B2* | 12/2013 | Drmanac et al. | 435/6.1 |
| 8,617,811 | B2* | 12/2013 | Drmanac | 435/6.1 |
| 8,673,562 | B2* | 3/2014 | Drmanac | 435/6.1 |
| 2009/0125246 | A1 | 5/2009 | Laza | |
| 2011/0033854 | A1 | 2/2011 | Drmanac | |
| 2011/0105353 | A1 | 5/2011 | Lo et al. | |

OTHER PUBLICATIONS

Halldorsson, B., et al., "Haplotype Phasing by Multi-Assembly of Shared Haplotypes: Phase-Dependent Interactions Between Rare Variants," Sep. 30, 2010, WSPC—Proceedings, pp. 88-99.

Ma, L., et al., "Direct determination of molecular haplotypes by chromosome microdissection," NIH Public Access Author Manuscript, Nat Methods, Apr. 2010, 7(4), [online], 7 pages.

Fan, H. C., et al., "Whole-genome molecular haplotyping of single cells," Nature Biotechnology Advance Online Publication, published [online] Dec. 19, 2010; retrieved from URL: http://www.nature.com/naturebiotechnology/, 9 pages.

Roach, J. C., et al., "Analysis of Genetic Inheritance in a Family Quartet by Whole-Genome Sequencing," Sciencexpress [online], Mar. 11, 2010, retrieved from URL: www.sciencexpress.org , 6 pages.

Kitzman, J.O., et al., "Haplotype-resolved genome sequencing of a Gujarati Indian individual," Nature Biotechnology, Jan. 2011, vol. 29, No. 1, published [online] Dec. 19, 2010, pp. 59-64.

Kizman, J.O., et al., "Supplementary Information for: Haplotype resolved genome sequencing of a Gujarati Indian individual," Nature Biotechnology, Jan. 2011, doi: 10.1038/nbt.1740, 20 pages.

Eskin, E., et al., "Large Scale Reconstruction of Haplotypes from Genotype Data," RECOMB'03, Apr. 10-13, 2003, Berlin, Germany, 10 pages.

Li, L. M., et al., "Haplotype Reconstruction from SNP Alignment," Journal of Computational Biology, 2004, vol. 11, Nos. 2-3, pp. 507-518.

McKernan, K. J., et al., "Sequence and structural variation in a human genome uncovered by short-read, massively parallel ligation sequencing using two-base encoding," Genome Res., published [online] Jun. 22, 2009, [retrieved on Aug. 24, 2011], retrieved from URL: genome.cshlp.org, 16 pages.

Niu, T., et al., "Bayesian Haplotype Inference for Multiple Linked Single-Nucleotide Polymorphisms," Am. J. Hum. Genet., 2002, vol. 70, pp. 157-169.

Bader, J. B., "The relative power of SNPs and haplotype as genetic markers for association tests," Pharmacogenomics, [online] 2001, vol. 2, No. 1, URL: http://www/Ashley-Pub.com, pp. 11-24.

Baumann, C., Determination of Haplotypes from Genotype information, © 2005 by Christiane Baumann, Informatik, ETH Zurich, 15 pages.

Christensen, et al. "Search for compound heterozygous effects in exome sequence of unrelated subjects," Genetic Analysis Workshop, BMC Proceedings, Oct. 13, 2010, vol. 5, Suppl. 9, 5 pages.

Pemberton, et al., "Inference of unexpected genetic relatedness among individuals in HapMap Phase III," The American Journal of Human Genetics, Oct. 8, 2010, vol. 87, pp. 457-464.

International Search Report and Written Opinion mailed Jan. 28, 2013 in PCT Application No. PCT/US2012/051825, 23 pages.

* cited by examiner

Reference for Chromosome (e.g. Chr 2)

Sequences of Copies of Chromosome from Sample

Parent1: C-CGCAG
Parent2: G-ATTTA

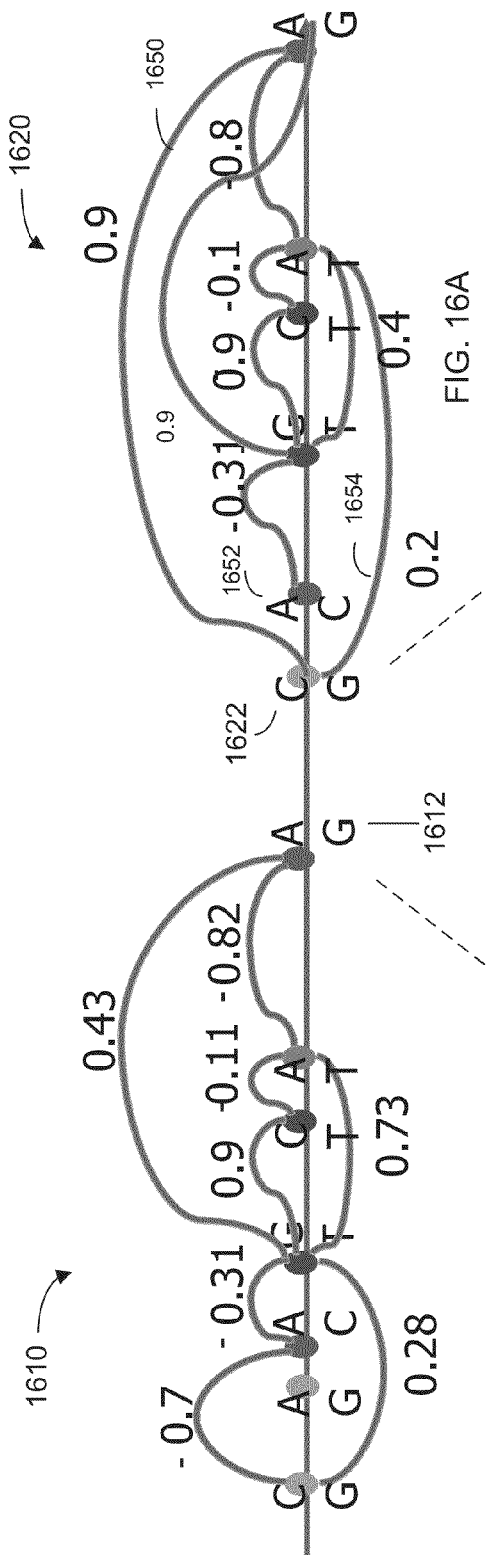
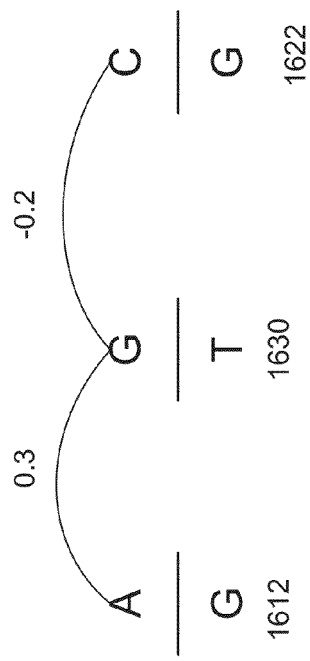
FIG. 16A
FIG. 16B

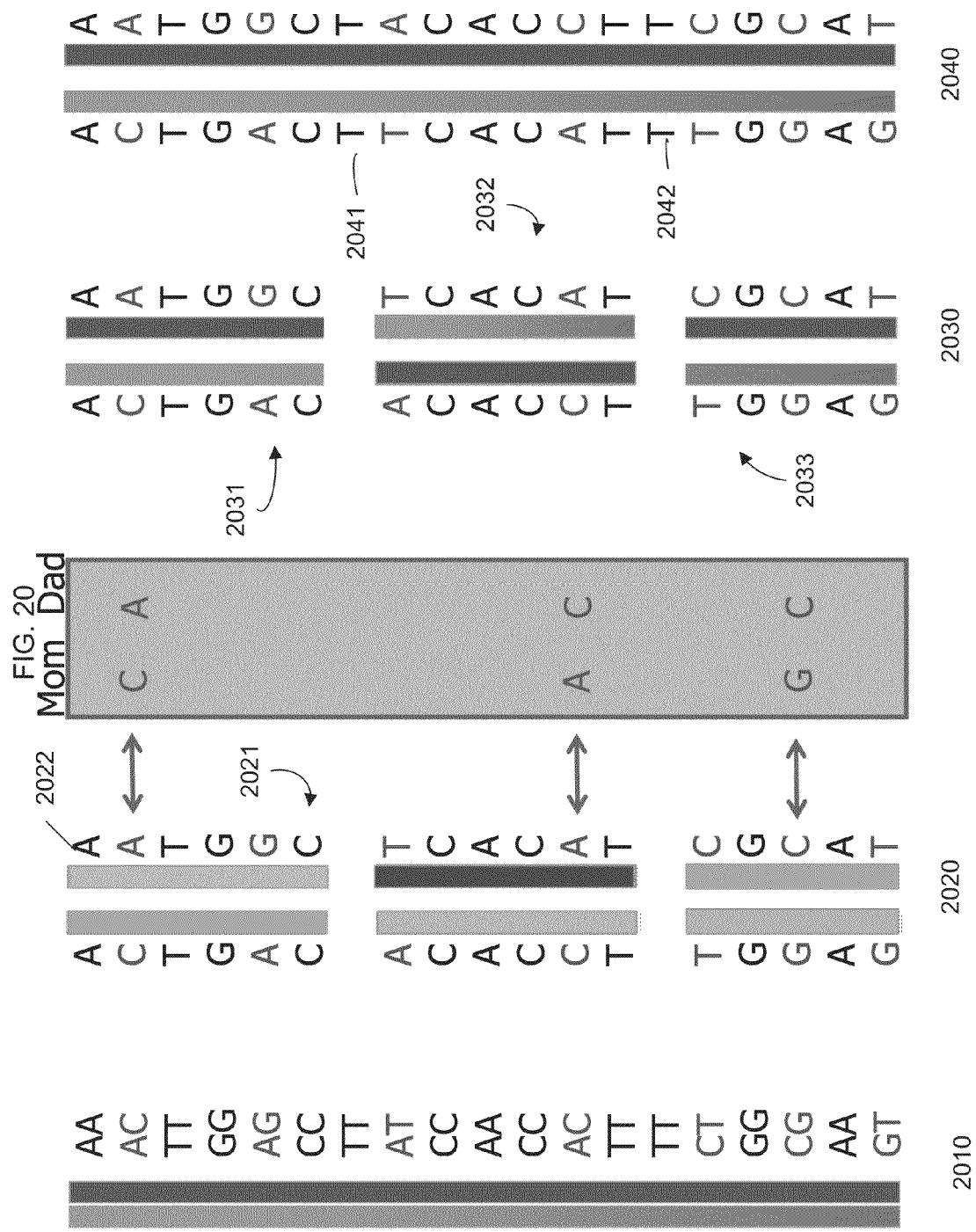

|   | A | C | G | T |
|---|---|---|---|---|
| A |   |   |   |   |
| C | 9 |   |   |   |
| G | 7 |   |   |   |
| T |   |   |   |   |

C A
G C (A in reality)

FIG. 21A

|   | A | C | G | T |
|---|---|---|---|---|
| A |   |   |   |   |
| C | 9 |   |   | 8 |
| G | 7 |   |   | 12 |
| T |   |   |   |   |

FIG. 21B

Strong Connectivity

|   | A | C | G | T |
|---|---|---|---|---|
| A |   |   |   |   |
| C | 15 |   |   |   |
| G |   |   |   | 9 |
| T |   |   |   |   |

Weak Connectivity

|   | A | C | G | T |
|---|---|---|---|---|
| A |   |   |   |   |
| C | 5 |   |   |   |
| G |   |   |   | 3 |
| T |   |   |   |   |

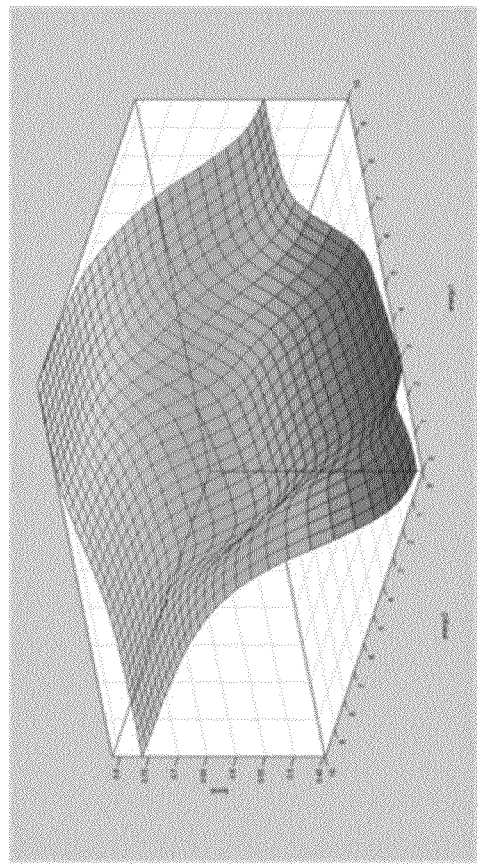 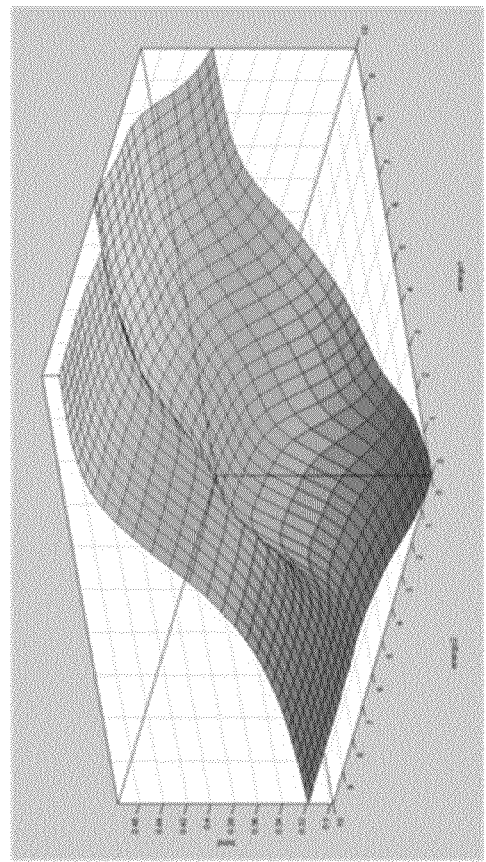
FIG. 23

Locus #2

|   | A | C | G | T |
|---|---|---|---|---|
| A | 0 | 9 | 12 | 0 |
| C | 0 | 0 | 1 | 0 |
| G | 0 | 0 | 0 | 0 |
| T | 0 | 0 | 0 | 1 |

Locus of interest

2400 — FIG. 24A

Locus #2

|   | A | C | G | T |
|---|---|---|---|---|
| A | 0 | 9 | 1 | 0 |
| C | 0 | 0 | 1 | 0 |
| G | 0 | 0 | 0 | 0 |
| T | 0 | 0 | 0 | 1 |

Locus of interest

2430 — FIG. 24B

Locus #2

2450

|   | A | C | G | T |
|---|---|---|---|---|
| A | 0 | 4 | 3 | 0 |
| C | 0 | 0 | 1 | 0 |
| G | 0 | 0 | 0 | 0 |
| T | 0 | 0 | 0 | 1 |

Locus of interest

FIG. 24C

ANALYZING GENOME SEQUENCING INFORMATION TO DETERMINE LIKELIHOOD OF CO-SEGREGATING ALLELES ON HAPLOTYPES

CROSS-REFERENCES TO RELATED APPLICATION

The present application claims priority from and is a nonprovisional application of U.S. Provisional Application No. 61/527,428, entitled "Analyzing Sequence Data For Determining And Combining Haplotypes" filed Aug. 25, 2011 by Kermani and Drmanac, the entire contents of which are herein incorporated by reference for all purposes.

This application is related to commonly owned and concurrently filed U.S. application Ser. No. 13/591,723, entitled "Phasing Of Heterozygous Loci To Determine Genomic Haplotypes" by Kermani and Drmanac, the disclosure of which is incorporated by reference in its entirety.

REFERENCE TO A "SEQUENCE LISTING," A TABLE, OR A COMPUTER PROGRAM LISTING APPENDIX SUBMITTED AS AN ASCII TEXT FILE

The Sequence Listing written in file-24-2.TXT, created on Oct. 2, 2012, 4,096 bytes, machine format IBM-PC, MS-Windows operating system, is hereby incorporated by reference in its entirety for all purposes.

BACKGROUND

The present invention is directed generally to genomic sequencing, and more specifically to efficiently obtaining accurate sequences of different haplotypes of a chromosome from a sequencing of a biological sample.

Current high-throughput genotyping technologies, when applied to DNA from a diploid individual, are able to determine which two alleles are present at each locus, but not the haplotype information (which combinations of alleles are present on each of the two chromosomes). Knowledge of the haplotypes carried by sampled individuals would be helpful in many settings, including linkage-disequilibrium mapping and inference of population evolutionary history, e.g., because genetic inheritance operates through the transmission of chromosomal segments and gene functionality loss.

The determination of the haplotype typically uses information from the general population, and not from data of the individual. For example, these methods work by applying the observation that certain haplotypes are common in certain genomic regions. Therefore, given a set of possible haplotype resolutions, these methods choose those that use fewer different haplotypes overall. Therefore, differences from the general population and specific recombinations are not identified, leading to these and other errors.

It is therefore desirable to provide methods of determining haplotypes of an organism (e.g. a person) from sequencing information of the individual that have increased accuracy, and can allow for efficient sequencing.

BRIEF SUMMARY

Embodiments can provide methods, systems, and apparatus for phasing of heterozygous loci to determine genomic haplotypes, universal phasing of DNA contigs to determine sequences of the parental transmitted chromosomes, and analyzing genome sequencing information to determine likelihood of co-segregating alleles on haplotypes.

Embodiments can provide methods, systems, and apparatus for determining haplotypes of one or more portions of a chromosome of an organism that is at least in part diploid or polyploidy from sequencing information of DNA or diploid RNA fragments. For example, locations in the genome where the genotype is known to be heterozygous can be used to determine the haplotype. The haplotype can be determined from an analysis that one allele on a first heterozygous locus is likely to be on the same haplotype as an allele on a second heterozygous locus. Such information can be used to define a connection between the two loci, with a particular orientation for which alleles are connected. 2-allele or longer haplotypes can be assembled through these connections. Errors in or lack of connection information can be identified through redundant connection information. The connections among a set of heterozygous loci can be analyzed to determine likely haplotypes for that set, e.g., an optimal tree of a graph containing the heterozygous loci.

Additionally, embodiments can provide a confidence value (strength) for a particular connection, which can be used to more easily identify errors. In one aspect, the confidence value can be obtained from data consistent with a particular connection and data inconsistent with a particular connection. Connection information can also be used for various types of loci to correct errors (e.g., in base calls). The connection information for non-hets can be combined with phased haplotypes in identifying errors and correcting them, filling in missing information, or confirming information, e.g., assessing a zygosity state (homozygous or heterozygous) or to call a base on a locus (e.g. using a het in close proximity to the locus).

Furthermore, embodiments can identify haplotypes of different contiguous sections (contigs) of the chromosome, and then match each haplotype of the contig to a particular chromosome copy (e.g., to a particular parental copy). Thus, an entire chromosome can be determined and the parental association can be established.

According to one embodiment, a method of determining at least part of a genome of an organism from one or more samples is provided, wherein the one or more samples include nucleic acid molecules of the organism. Sequencing information of nucleic acid molecules is received. A plurality of loci of a first chromosome are identified. A first strength conveys a likelihood that a first allele of a first locus and a second allele of a second locus are on a first 2-allele haplotype of the organism. A computer system computes the first strength includes determining a first positive contribution based on sequencing information consistent with the first allele and the second allele being on the first 2-allele haplotype, and determining a first negative contribution based on sequencing information inconsistent with the first allele and the second allele being on the first 2-allele haplotype. The first positive and first negative contributions are then used to compute the first strength. Two haplotypes involving the first locus and the second locus are calculated using the first strength. For example, base calls can be corrected or validated or determined. As another example, haplotypes can be phased, as may be done with a minimum spanning tree.

Other embodiments are directed to systems and computer readable media associated with methods described herein.

A better understanding of the nature and advantages of the present invention may be gained with reference to the following detailed description and the accompanying drawings.

BRIEF DESCRIPTION OF THE DRAWINGS

FIG. 7A shows a connectivity matrix 700 for a locus #1 and a locus #2 according to embodiments of the present invention. FIG. 7B shows a connectivity matrix 730 where locus #1 is likely homozygous for the nucleotide C according to embodiments of the present invention. FIG. 7C shows a connectivity matrix 770 for determining a connection of alleles at locus #1 and locus #2 according to embodiments of the present invention.

FIG. 16A shows graphs of two separated contigs according to embodiments of the present invention. FIG. 16B shows an example of connection information having a low strength in a region between the final and beginning hets to two separate graphs according to embodiments of the present invention.

FIG. 20 shows an illustration of showing a process of universal phasing for a reference genome 2010 (SEQ ID NOS:1 and 2) according to embodiments of the present invention, Haplotypes 2040 combined from contigs 2030=SEQ ID NOS:3 and 4.

FIGS. 21A-21D show example connectivity matrices analyzed for phasing haplotypes according to embodiments of the present invention.

FIG. 23 shows output curves for determining strength values according to embodiments of the present invention.

FIGS. 24A-24C show example connectivity matrices analyzed for confirming or correcting base calls according to embodiments of the present invention.

DEFINITIONS

Figure 1:
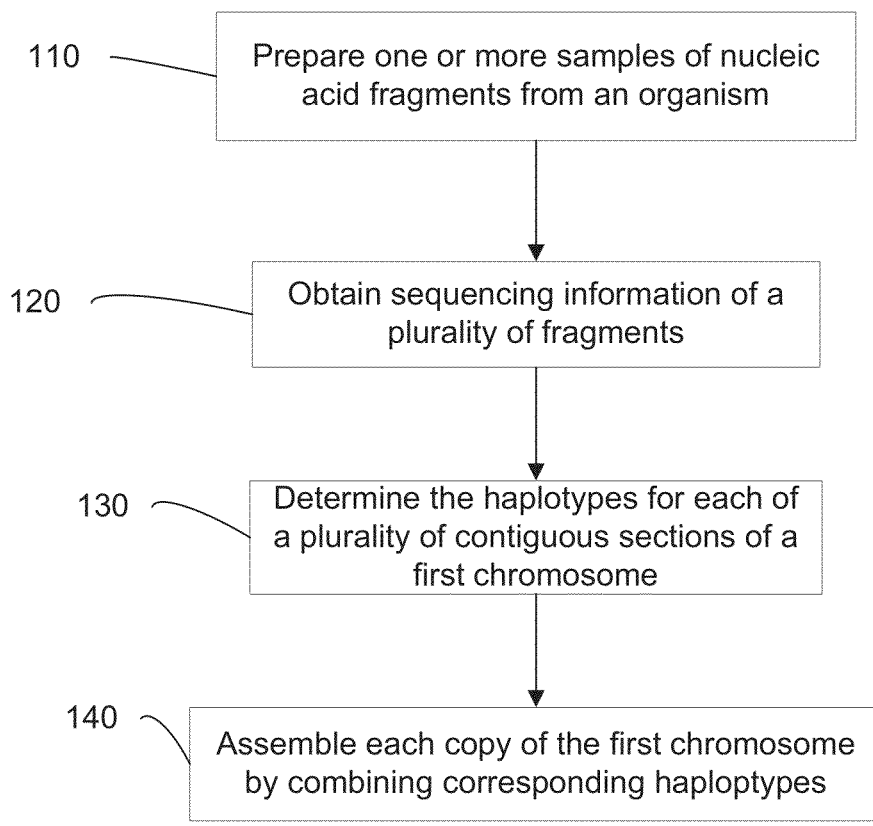
FIG. 1 is a flowchart for determining haplotypes for a chromosome according to embodiments of the present invention.

The following definitions may be helpful in providing background for an understanding of embodiments of the invention.

"Polynucleotide", "nucleic acid", "oligonucleotide", "oligo" or grammatical equivalents used herein refers generally to at least two nucleotides covalently linked together in a linear fashion. A nucleic acid generally will contain phosphodiester bonds, although in some cases nucleic acid analogs may be included that have alternative backbones such as phosphoramidite, phosphorodithioate, or methylphophoroamidite linkages; or peptide nucleic acid backbones and linkages. Other analog nucleic acids include those with bicyclic structures including locked nucleic acids, positive backbones, non-ionic backbones and non-ribose backbones.

The term "reference polynucleotide sequence", or simply "reference", refers to a known sequence of nucleotides of a reference organism. The reference may be an entire genome sequence of a reference organism, a portion of a reference genome, a consensus sequence of many reference organisms, a compilation sequence based on different components of different organisms, a collection of genome sequences drawn from a population of organisms, or any other appropriate sequence. The reference may also include information regarding variations of the reference known to be found in a population of organisms. The reference organism may also be specific to the sample being sequenced, possibly a related individual or the same individual, separately drawn (possibly normal to complement cancer sequence).

"Sample polynucleotide sequence", or simply "sample sequence", refers to a nucleic acid sequence of a sample or target organism derived from a gene, a regulatory element, genomic DNA, cDNA, RNAs including mRNAs, rRNAs, siRNAs, miRNAs and the like and fragments thereof. A sample polynucleotide sequence may be a nucleic acid from a sample, or a secondary nucleic acid such as a product of an amplification reaction. For a sample polynucleotide sequence or a polynucleotide fragment to be "derived" from a sample polynucleotide (or any polynucleotide) can mean that the sample sequence/polynucleotide fragment is formed by physically, chemically, and/or enzymatically fragmenting a sample polynucleotide (or any other polynucleotide). To be "derived" from a polynucleotide may also mean that the fragment is the result of a replication or amplification of a particular subset of the nucleotide sequence of the source polynucleotide.

As used herein, a "fragment" refers to a nucleic acid molecule that is in a biological sample. Fragments can be referred to as long or short, e.g., fragments longer than 10 Kb (e.g. between 50 Kb and 100 Kb) can be referred to as long, and fragments shorter than 200 bases can be referred to as short. Embodiments can perform paired-end sequencing of fragments to obtain a left arm read and a right arm read for each fragment. Other embodiments can just perform a single arm read. As used herein, a "mate pair" or "mated reads" refers to the right arm and left are also called a mate pair. "Mapping" refers to a process which relates an arm read (or a pair of arm reads) to zero, one, or more locations in the reference to which the arm read is similar, e.g., by matching the instantiated arm read to one or more keys within an index corresponding to a location within a reference.

As used herein, an "allele" corresponds to one or more nucleotides (which may occur as a substitution or an insertion) or a deletion of one or more nucleotides. A "locus" corresponds to a location in a genome. For example, a locus can be a single base or a sequential series of bases. A "heterozygous locus" (also called a "het") is a location in a reference genome or a specific genome of the organism being mapped, where the copies of a chromosome do not have a same allele (e.g. a single nucleotide or a collection of nucleotides). A "het" can be a single-nucleotide polymorphism (SNP) if the location has two different alleles. A "het" can also be a location where there is an insertion or a deletion (collectively referred to as an "indel") of one or more nucleotides or one or more tandem repeats. A "candidate het" is a locus that is (e.g. by a confirmation process) or might be a het. As used herein, the term "chromosome" includes copies of DNA (e.g., as occur in animals) or copies of RNA (e.g., as may occur in viruses).

A "connection" between a pair of hets exists when sequencing information suggests that an allele of the first het is on the same copy (haplotype) of the chromosome as an allele of the second het. If two alleles are on the same haplotype, then the alleles are said to be "linked". If a connection exists, the "orientation" of a connection can specify which alleles of the first het are connected with which alleles of the second het. A connection can have a "strength", which can convey a confidence that the connection is correct. For example, the connection strength can provide a measure of a likelihood that certain alleles of a pair of candidate hets are on a same haplotype of the first chromosome. The strength of a possible connection can confirm that the connection actually exists, e.g., using a threshold. In various embodiments, a higher strength can convey higher confidence or a lower strength can convey higher confidence (e.g., depending on the mathematical formulation).

A set of hets can comprise a "graph" of interconnected hets. The interconnected hets of a "graph" can define a contiguous section (contig) of a chromosome, where a contig would have two haplotypes for a diploid organism. A "tree" is a collection of connections in which any two hets are connected by exactly one simple path, where a "path" is one or more connections between the two hets.

DETAILED DESCRIPTION

Present method for determining a sequence of a chromosome are inaccurate, e.g., since many approximations are made. However, current methods for gaining accuracy are simply to perform extraordinary amount of sequencing operations. Accordingly, accurate and efficient methods of sequencing a genome from a biological sample are desired.

In some embodiments, locations in the genome where the genotype is known to be heterozygous can be used to determine the haplotype. The haplotype can be determined from an analysis that one allele on a first heterozygous locus is likely to be on the same haplotype as an allele on a second heterozygous locus. Such information can be used to define a connection between the two loci, with a particular orientation for which alleles are connected. Errors can be identified through redundant connection information. Additionally, a confidence value (strength) for a particular connection can be used to more easily identify errors. The connections among a set of heterozygous loci can be analyzed to determine a likely haplotype for that set, e.g., an optimal tree of a graph containing the heterozygous loci.

Furthermore, some embodiments can identify haplotypes of different contiguous section (contig) of the chromosome, and then match each haplotype of the contig to a particular chromosome copy (e.g., to a particular parental copy). Thus, an entire chromosome can be determined and the parental association can be established. The parental information can help segregate all chromosomes of each parent, and also find the exact transmission from each parent.

I. Overview

FIG. 1 is a flowchart for determining haplotypes for a chromosome according to embodiments of the present invention. Greater detail of certain parts of various embodiments are described in other sections.

In step 110, one or more samples of nucleic acid fragments from an organism are prepared. For example, a sample of blood, saliva, tissue, urine, or other sample derived from a body could be used. Some embodiments can also be used to determine a part of a genome of plants and other types of organisms, such as viruses. A sample can be separated into smaller parts, e.g., aliquots, which can then be separated into smaller constituent parts, such as wells on a silicon wafer.

Besides physical separation, the samples can be refined from an original sample taken from the organism. Such refinement can include the creation of DNA NanoBalls (DNB). In one embodiment, a DNB can result from the two ends of a fragment being chopped off and rejoined to create a circular that includes nucleic acids from DNA or RNA of the organism. The circular molecule can then be replicated in a long strand. The fragments can also be tracked to a same aliquot, where a long fragment can be broken down into smaller fragments that are later sequenced, at least partially. Such tracking can provide information as to the original longer fragment before the aliquot is formed. For example, before a mixture (e.g. a solution) is dispensed from a pipette, which can cause a longer fragment of nucleic acid molecules to break into smaller fragments.

In step 120, sequencing information of a plurality of fragments is obtained. The sequencing can be performed in any suitable manner. For example, a DNB can contain adapters that have been inserted into fragments at select points.

Labeled probes can be attached to determine particular bases at locations relative to the adaptor. In this manner, the two ends of a fragment can be sequenced, and are called arm reads (only one arm read could also be obtained, which can include a whole fragment). These arm reads can be aligned to a reference genome to determine a mate pair, with sequence information between the two arm reads potentially being inferred from the reference genome. The mapping of the two arm reads can be constrained by an expected length of a fragment, e.g., the two arm reads cannot map to two genomic locations that are very far away from each other (such mappings would be unlikely to occur from a same fragment).

Other embodiments for obtaining sequencing information are described herein. For example, long fragment read (LFR) techniques can match arm reads of different fragments as being likely from a same longer fragment that had been broken up into smaller fragments, from which the sequenced arm reads were taken.

In step 130, the haplotypes for each of a plurality of contiguous sections of a first chromosome are determined. These contiguous sections (contigs) of the first chromosome and the haplotypes of them can be determined in various ways. Certain embodiments are directed to ways of determining the haplotypes. One embodiment determines the haplotypes of a contig by phasing the loci that are determined to be heterozygous for the genome being analyzed. Other embodiments for determining the haplotypes of a contiguous section of the genome include clustering mate pair reads of a same fragment that aligns to the contiguous section.

The fact that a single contiguous section of the whole first chromosome is not known at this point can result for one or more reasons. For example, as the DNA or RNA strands of the original sample become broken at various stages in the process, a single sequence of the chromosome is not obtained. Thus, when a fragment is sequenced (e.g., its two ends are sequenced) one does not know which copy of the first chromosome the fragment originated. However, step 130 can determine which sequence information is likely from a same part (section) of a same copy of the chromosome, thereby determining haplotypes (e.g. the two haplotypes for a diploid or polyploid organism) for the contig. Although, which haplotypes of one contig are on the same chromosome copy as the haplotypes of another contig are not known at this point.

In step 140, each copy of the first chromosome is assembled from the respective haplotypes of the various contiguous. Which haplotypes of one contig correspond to which haplotypes of other contigs can be determined, e.g., through a universal phasing. The corresponding haplotypes can then be combined to determine each copy of the chromosome. In one aspect, the determined sequence of each copy of the chromosomes can be based on one or more reference chromosomes to fill in parts that were not actually sequenced for the organism being tested. Population genetics could also be used to link contigs to get longer contigs.

II. Hets and Connections

A. Heterozygous Locus (Het)

This section introduces some concepts that will be useful in describing embodiments for contig phasing. Many locations in a genome have a same nucleotide base (A, C, G, or T) in each copy of a chromosome. Such locations are homozygous for a particular base. However, some locations are heterozygous in that the chromosome copies have different bases at the location. More generally, a "locus" can refer to one location or a sequential series of locations, and an "allele" can refer to one base, multiple bases, an addition of bases, or a deletion of bases. A heterozygous locus is also called a "het". A single nucleotide polymorphism SNP is an example of a het.

A reference genome can show loci that are commonly heterozygous ("candidate hets"). As mentioned above, a reference genome can be used to determine a likely location of a fragment in the genome, e.g., by aligning both or just one of the arm reads at the ends of the fragment to the reference genome. The read sequences of the fragment can be placed in a particular location of the genome, even if the read sequences have some differences from the reference genome. Areas of the sample genome that are not sequenced can also be filled in by parts of the reference genome.

Figure 2A:
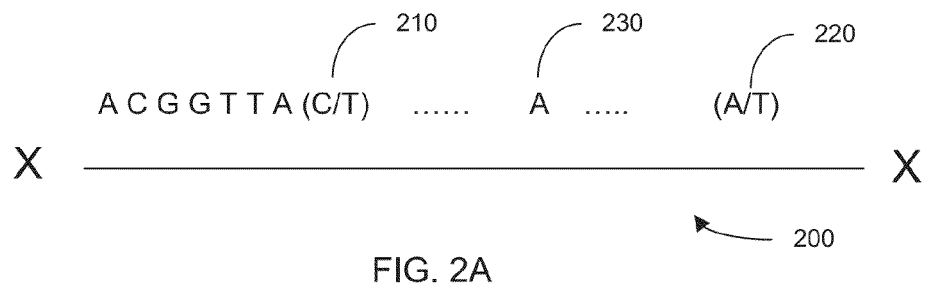
FIG. 2A shows a reference genome 200 for a first region of a particular chromosome according to embodiments of the present invention.

FIG. 2A shows a reference genome 200 for a first region of a particular chromosome according to embodiments of the present invention. The X marks show the beginning and end of the first region, which can be considered a contiguous section (contig) of the genome. Reference genome 200 can be calculated from a plurality of genomes (e.g., genomes of 6 people). Reference genome 200 shows common nucleotides at the various locations of the first region of chromosome. In some instances, more than one nucleotide may commonly occur. For example, location 210 shows that C and T occur often enough in the sampled population for that location in the reference genome represents to be marked with the two nucleotides. Location 210 would be a candidate for a "het" in the genome of the sample being currently sequenced.

Since different nucleotides occur, an organism can have one nucleotide on one copy of the chromosome, and a different nucleotide at another copy of the chromosome (humans normally have two copies of chromosomes 1-22). In one embodiment, a probability of each allele at a candidate het can be provided, e.g., as a percentage. A threshold probability can be required for a location to be marked as commonly having more than one possible allele. In one implementation, there can be a major and minor allele (or more variations) at each het.

Figure 2B:
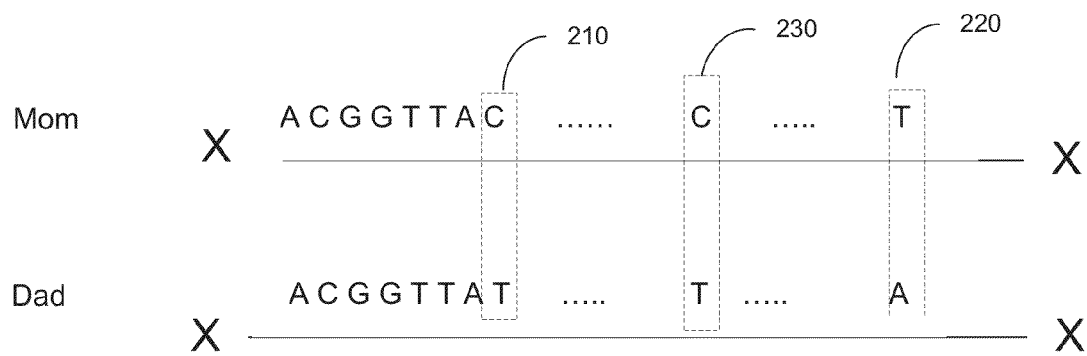
FIG. 2B shows the sequences of two copies of the chromosome for particular individual according to embodiments of the present invention.

FIG. 2B shows the sequences of two copies of the chromosome for particular individual according to embodiments of the present invention. Each copy is marked as being from the mother (Mom) or father (Dad) of the individual, since each copy is normally from one of the parents. The copy of a chromosome can be called a haplotype. Also, just part of a copy of the chromosome can be called a haplotype. FIG. 2B shows a result that can be obtained from embodiments, and is shown as such to illustrate hets and haplotypes.

As shown, location 210 has C on one copy and T on the other copy, which reference genome 200 had shown was a possibility. Thus, candidate hets and actual hets can be determined and/or confirmed from the sample genome. Similarly, location 220 shows a candidate het that was confirmed to be in the sample genome. Note that the order in the reference genome (e.g., A/T) does not prescribe which chromosome (i.e. mom or dad) that the nucleotides will appear.

A het can also be identified from the sequencing of the sample, for example, where the reference genome is not known to commonly have different nucleotides. For example, location 230 exhibits C/T for the sample, whereas the reference genome exhibits just one nucleotide (A). Accordingly, location 230 shows a het that was not identified as a candidate in reference genome 200, but is indeed a het in the genome of the sample being presently mapped.

In one embodiment, a het can be confirmed from sequencing data of the sample genome in that a same location can show substantial amounts of two or more alleles. For example, the sequence information from a sample would show the bases measured at locus 210 to be C and T, both in appreciable amounts. However, the fact that locations 210 and 220 have C and T on the same haplotype is normally not plainly evident from the sequencing information, but an analysis of the sequencing information can convey such knowledge.

B. Pair-Wise Connections of Heterozygote Loci (Hets)

In theory, each of the actual hets on a chromosome are connected to each other. However, connections can be difficult to determine, particularly with limited sequencing information. For example, two hets that are far away will usually not be on a same fragment, because no fragments will ever be that long. Additionally, not every het will connect to the next het, e.g., as the distance could be too long. A connection between two hets can be determined when there is evidence of an allele of one het being on the same copy of a chromosome as an allele of the other het. In one aspect, a genome typically has hets on average 1 every 1500-2000 bases. However, the distance between two specific sequential hets could be smaller or larger, by as much as a factor of ten.

Looking back at FIG. 2A or 2B, loci 210-230 typically do not all appear in a sequence of a same fragment, particularly using short read techniques typical of paired-end sequencing. For example, loci 210-230 are typically separated by hundreds of bases for candidate hets, although for some regions the separation can be in the thousands. The raw sequencing information typically shows that more than one allele is possible at certain loci, and thus that there are different possibilities for the haplotypes of those loci.

For example, if we look at the candidate hets 210 and 230 on the reference chromosome, this information does not convey which chromosome copy that each nucleotide is on. Simply looking at the reference chromosome or some raw sequencing information, the copy from the mom could have a C at location 210 and a T at location 230. If each location really had two options, there would be 4 different possibilities for the two locations, CC, CT, TC, and TT for each copy. If the two locations are actually heterozygous at the two locations in the sample, then there are only two possibilities, e.g., since locus 210 cannot have C for both haplotypes of the contiguous section shown. Ignoring the labels of mom or dad, one possibility is that one haplotype has CC and the other haplotype has TT. The other possibility is that one haplotype has CT and the other haplotype has TC.

Which possibility is more likely can be determined through a concept of pair-wise connections of the hets. Connections may occur because there may be particular haplotypes that are commonly found. For example, in FIG. 2B, it may be known that CC may be found commonly on the same haplotype for the first region of the chromosome, and thus C at loci 210 and C at 230 may be pair-wise connected. This connection may occur when the locations are close enough that any rearrangements (also called recombinations) of the genome typically occur at points (e.g. marked as X for a hotspot) that are outside of the first region.

Such recombinations can occur among the two chromosomes of a parent, and thus the chromosome contributed by the parent will not be exactly the same as one of the chromosomes of the parent. Therefore, there may be two hets that are connected in some persons, but not connected in the sequencing information of a person where recombination has occurred between the two hets. Such recombinations can make it difficult to determine a haplotype of a person, since the recombination would be different than what is common.

Although connections between hets can be inferred from genomes of other organisms, some embodiments identify connections from the sequencing information of the sample. For example, it is possible that the sequenced arm reads of the two ends of a fragment happen to fall on loci 210 and 230 respectively. Thus, the sequenced alleles at the loci 210 and 230 can be considered to be linked as being on a same haplotype. Such a data point of a particular allele at locus 210 linked to a particular allele at locus 230 can be used to determine whether the sequencing information shows a connection (e.g., within a sufficient level of likelihood) between the loci 210 and 230. Other examples for determining a data point for a connection are described in more detail below. In one aspect, connections are investigated for loci within a specified range (e.g., 10 kb) of each other.

C. Orientation of Connections

In one embodiment, if a connection is determined to exist between two loci (e.g. between respective alleles of two candidate hets), then the two loci can be identified as being heterozygous loci. As mentioned above, if an analysis of the sequencing information of a sample shows that the two heterozygous loci each have two possible alleles, there are two possibilities for the connection for two haplotypes. Each possibility is called an orientation, herein.

Figure 3:
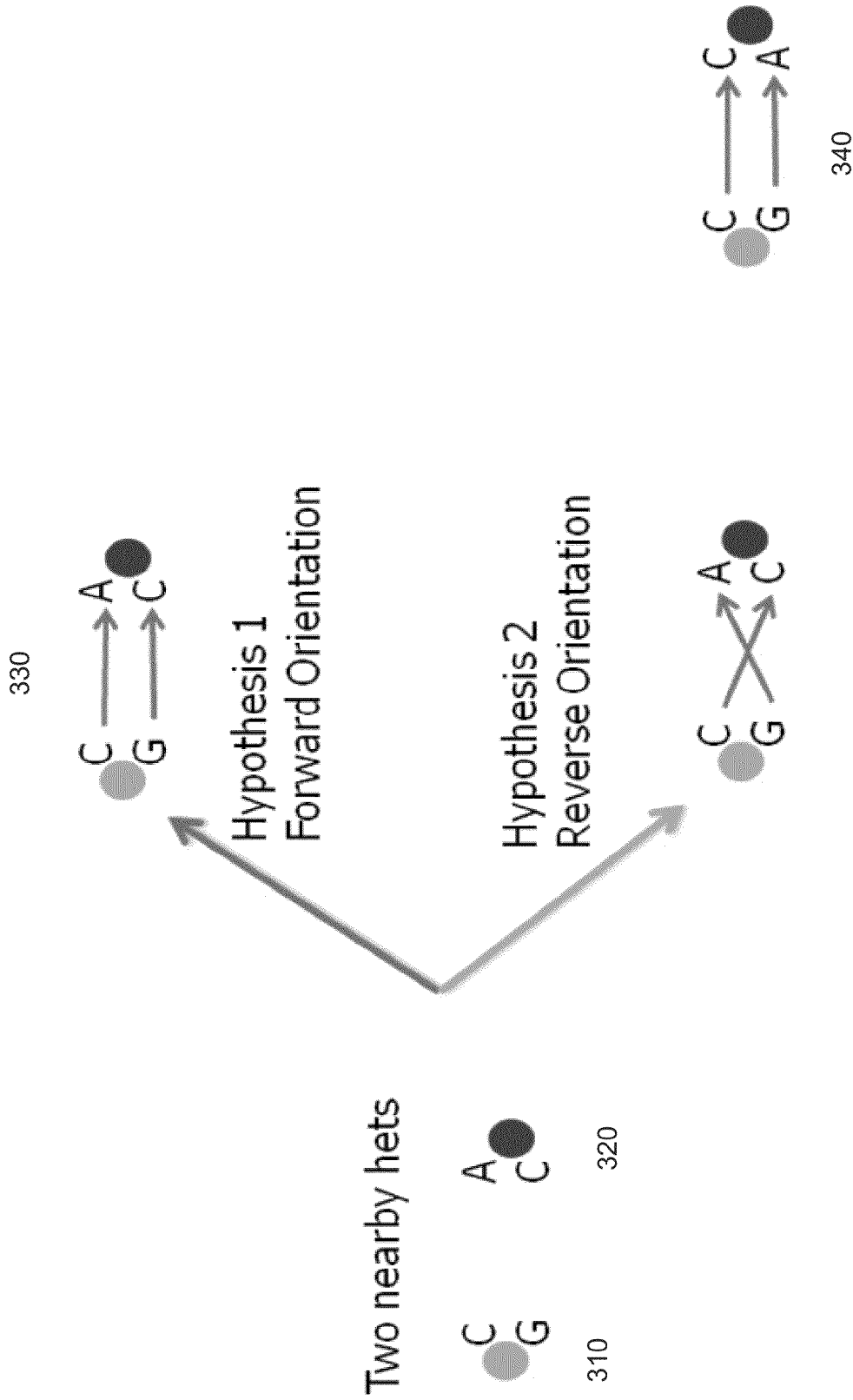
FIG. 3 is a diagram illustrating the two orientations for a connection between two hets according to embodiments of the present invention.

FIG. 3 is a diagram illustrating the two orientations for a connection between two hets according to embodiments of the present invention. As shown, two loci are determined to be hets. A first het 310 is determined to have alleles C and G. A second het 320 is determined to have alleles A and C. The two possibilities are that C at locus 310 is connected to A or C at locus 320. If C at locus 310 is found to be connected (e.g. according to some criteria) to A at locus C, then the two alleles are linked and are determined to be on a same 2-allele haplotype, as is defined as a particular orientation of the connection between loci 310 and 320. The other 2-allele haplotype of G at locus 310 and C at locus 320 would correspond to the same orientation, which is shown to have a pair of 2-allele haplotypes.

In some embodiments, two hypotheses can be formed to test which possibility is more likely. This test may be performed without first determining whether there is a connection between two loci. Evidence, which may also include counterevidence, can be evaluated for each of the two connection hypothesis.

As shown, the first hypothesis (forward orientation) is that C at het 310 is linked (also referred to as "connected") to A at het 320, which would then mean that G at het 310 is linked with C at het 320. Evidence for both links can be required for a hypothesis. As a matter of convention, the nucleotides are shown in alphabetical order, and a forward orientation is when the top allele at one het is linked to a top allele of a second het. A similar convention can also be used when an allele is something besides a nucleotide (e.g. an insertion, deletion, or group of bases). Thus, a forward orientation would indicate that C at het 310 and A at het 320 are both on a first 2-allele haplotype, and that G at het 310 and C at het 320 are both on a second 2-allele haplotype, as is shown at 330.

The second hypotheses (reverse orientation) is that C at het 310 is linked to C at het 320, which would then mean that G at het 310 is linked with A at het 320. Thus, a reverse orientation would indicate that C at het 310 and C at het 320 are both on a first 2-allele haplotype, and that G at het 310 and A at het 320 are both on a second 2-allele haplotype, as is shown at 340. In one embodiment, a forward orientation can be designated as positive and a reverse orientation can be designated as negative.

Embodiments can test the different hypotheses in various ways. Some examples are described in more detail below. In some embodiments, a strength is determined for each hypothesis, and the hypothesis with the larger strength is chosen as the winning hypothesis. For example, the number of times that two alleles appear on a same fragment can be used to determine a strength of a particular orientation. In one embodiment, the strength can also be used to determine whether a connection actually exists, e.g., a strength can be required to be greater than a threshold for a connection to exist. Such a strength can also be used in comparing connections to each other, e.g., to resolve conflicting connections, as will be described later. In one implementation, if a candidate het is determined to have no connections, then it can effectively not be considered a het, even though it could be a singleton het, i.e., separated from other hets by a far distance on both sides.

D. Connection Among Neighboring Loci

The determination of connections and the corresponding orientation can be performed for a plurality of different candidate hets across a chromosome. As described in the next section, these connections can be used to determine haplotypes for contiguous sections of a chromosome or for the entire chromosome. In one embodiment, only certain connections are investigated. For example, a cutoff for can be used so that only candidate hets that are near each other are investigated. In one aspect, these pairs of candidate hets are ones where a connection might be expected. In various embodiments, the cutoff can specify the number of heterozygous loci (e.g. 100) within which to check, and/or within a number of base pairs (e.g., 10 Kb, 20 Kb, or 50 Kb).

In one embodiment, a sparse matrix can be determined. In one aspect, such a sparse matrix can be an upper (or lower) triangular matrix, with the dimensions being a number of a candidate het. A very first locus in the matrix (e.g., if the candidate het closest to an end of the chromosome) can have connections to the hets numbered 2 to 101 (e.g. if the cutoff is to be within 100 hets), corresponding to matrix elements (1,2) to (1,101). The values of the matrix outside of this cutoff would necessarily be zero. Some matrix elements within (1,2) to (1,101) could also be zero if a determination shows that no connection exists, e.g., (1,50) could be zero.

In various embodiments, the non-zero matrix elements can be positive or negative depending on the particular orientation of the connection, the non-zero elements can be restricted to binary (e.g. 0 no connection and 1 being a connection), and the non-zero elements can have real values. In one implementation, a real value (such as a non-integer value) can result from multiplying an integer contribution to a matrix element (e.g., resulting from a measurement for fragment from a particular aliquot) by a weighting factor. The weighting factor can be associated with an accuracy of a particular measurement. In one embodiment, the use of positive and negative can be combined with the binary or real values to provide orientation and connection information in a same matrix element. The sparse matrix can be stored in various ways, as will be known to one familiar with sparse matrices. In one aspect, a sparse matrix is an efficient way to implement a graph, e.g., as is described in more detail below.

III. Phasing Contigs

Phasing can analyze the connection information to determine the haplotypes within a particular region. Certain embodiments can use the connections between hets and the determined orientations to determine a haplotype of a contiguous section of a chromosome or an entire chromosome. For example, methods can determine which alleles of each het of a group of hets are on a same copy of the chromosome.

Figure 4:
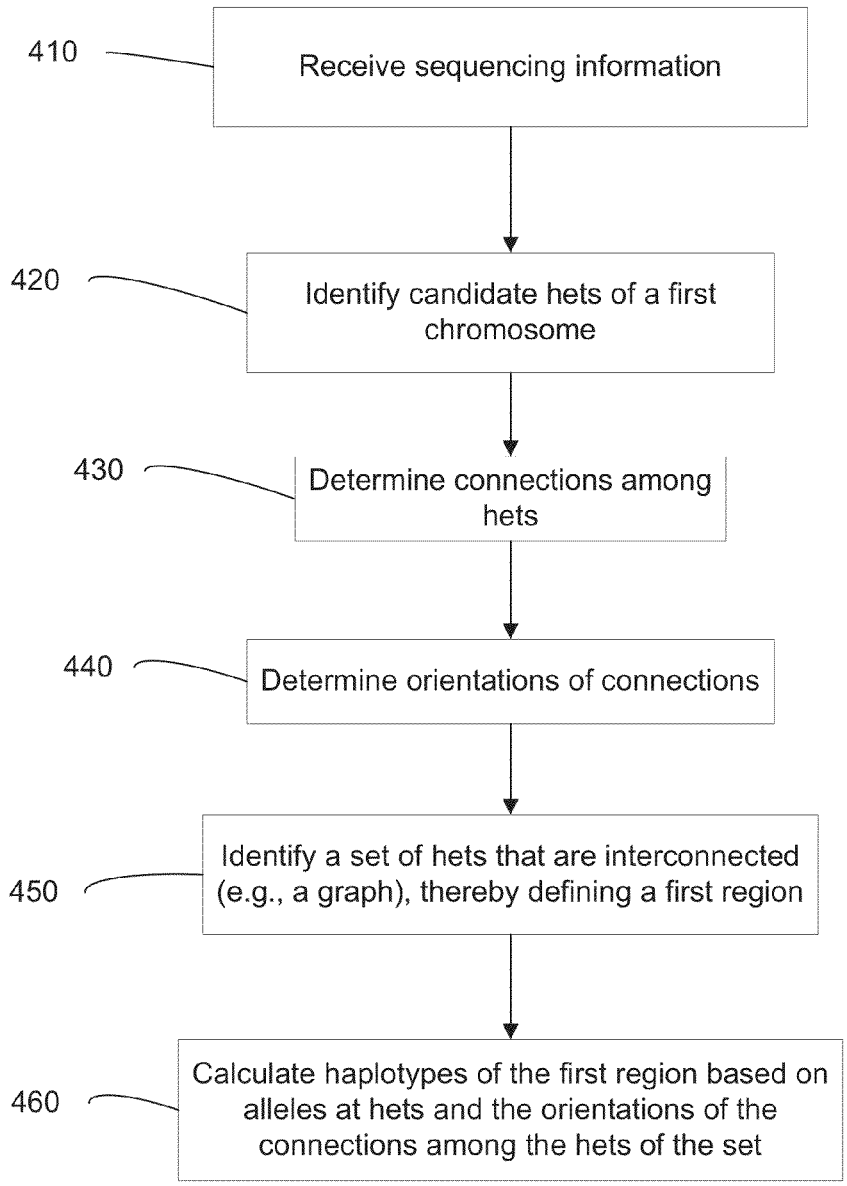
FIG. 4 is a flowchart illustrating a method 400 of determining at least part of a genome of an organism from one or more samples according to embodiments of the present invention.

FIG. 4 is a flowchart illustrating a method 400 of determining at least part of a genome of an organism from one or more samples according to embodiments of the present invention. The one or more samples include nucleic acid molecules of the organism. For example, two haplotypes can be determined for at least a portion of a chromosome. In one embodiment, method 400 can be used for step 130 of method 100. Greater detail of certain parts of various embodiments are described in other sections.

In step 410, sequencing information of a plurality of the nucleic acid molecules in the one or more samples is received. The sequencing information can have many forms. In one embodiment, the sequencing information includes two arm reads for each nucleic acid molecule (also called a fragment). These arm reads can include which nucleotide was measured at each location near each end of a fragment (e.g., ~35-39 nucleotides at each end of the fragment). These arm reads can be used to align the fragment to locations in the genome, e.g., using a reference genome.

In step 420, a plurality of candidate hets are identified for a first chromosome. In one embodiment, a candidate het is a locus identified as having or potentially having two or more different alleles. Candidate hets can be identified as described herein, e.g., from the reference genome and/or the sequencing information. Candidate hets can also be identified from a file read in by a computer system, where the file specifies candidate hets. In one implementation, the sequencing information can include multiple arms reads that align to a same locus. Among the multiple arm reads, more than one allele can be measured at a particular locus, which can thus indicate a candidate het. In various embodiments, a threshold can exist for the number of second alleles to show up before a locus is considered a candidate het, as well as before a candidate het is considered a het. The first chromosome can be any of the chromosomes.

In step 430, connections are determined among hets. In one implementation, it can be determined whether each candidate het connects with each of one or more other candidate hets based on the sequencing information. If a candidate het is tested for a connection to each of multiple candidate hets, the redundant information may be obtained, which can be used to fill in missing connections or identify conflicting connections (e.g. incorrect information).

Each such pair-wise connection can specify a first heterozygous locus having two alleles that connect respectively with two alleles of a second heterozygous locus. Various embodiments can use different information to interpret that alleles at two hets are from a same fragment, and thus are connected (e.g., from arm reads of a same fragment or from two arm reads originating from a same well, as is described later). Each data point showing alleles of the two hets to be from the same fragment can be considered in determining whether a connection does indeed exist. In one embodiment, once a connection is determined between two candidate hets, the candidate hets can be considered hets.

In step 440, an orientation between the pair of heterozygous loci of each connection is determined. In one aspect, the orientation specifies which allele of the first heterozygous locus is connected with a first allele of the second heterozygous locus. In one embodiment, one can determine which orientation is more likely from the sequencing information, e.g., which orientation has more data points consistent with that orientation.

In one embodiment, the determination of the orientation and the determination of whether a connection exists can be performed at the same time. For example, one can determine which orientation is more likely for a particular pair of candidate hets from the sequencing information, and then determine that a connection exists only if the more likely orientation is itself likely enough (e.g. by comparing a strength of the more likely orientation to a threshold), as is described in more detail below. Accordingly, if one determined that a first allele on a first het was sufficiently linked to a second allele on a second het, which effectively determines a 2-allele haplotype, then such a step determines that a connection exists between the two hets and determines the orientation (i.e. an orientation that includes the first allele and the second allele on the same haplotype).

In step 450, a first set of at least three heterozygous loci that are interconnected. The connections to each other can be direct (e.g., via since pair-wise connection) or via one or more intermediate connections. Thus, one could start from any heterozygous locus of the set and reach any other heterozygous locus of the set along connections. The set of all connection among the hets of the set can be considered as a single graph. In various embodiments, the number of heterozygous loci can be at least 6, at least 8, at least 10, at least 20, at least 30, and at least 100.

This first set of heterozygous loci can define a first region of the first chromosome. In one embodiment, this first region is a contiguous section of the first chromosome. The first region can be the genome between a first het of the set and a last het of the set when the hets are presented in order.

In step 460, the haplotypes of the first region are calculated based on the two alleles of each heterozygous locus in the first set and the orientations of the connections among the heterozygous loci in the first set. For example, a first het closest to an edge of the first region can be used as a starting place. An orientation of a first connection to a second het can be used to determine which alleles are on a same haplotype. The orientation of a second connection from the second het to a third het can be used to determine which alleles on the third het are on a same haplotype as those of the first and second het, and so on, until the haplotype is determined from all of the hets in the set.

Figures 5A, 5B:
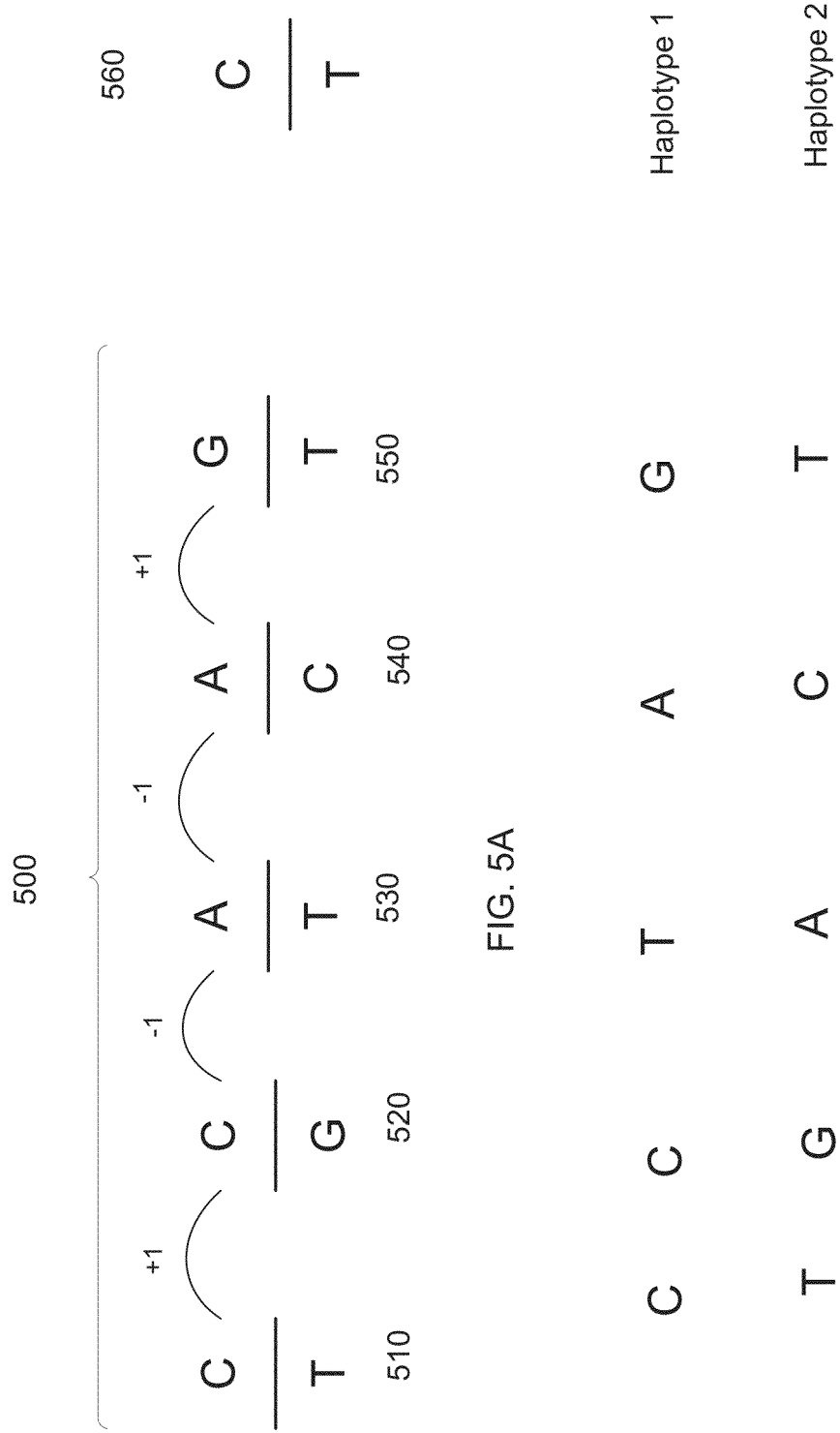
FIGS. 5A and 5B show a simplified example of an application of method 400 according to embodiments of the present invention.

FIGS. 5A and 5B show a simplified example of an application of method 400 according to embodiments of the present invention. FIG. 5A shows a plurality of hets. The first five hets are connected to form a set 500, where each het of the set is connected to at least one other het in the set. Note that other bases exist between these hets, but are not shown for ease of presentation. In the example shown, each het of set 500 is connected to only one other het in the same direction, and thus a het is connected to two other hets at most. However, other examples can have more than one connection in a given direction, thereby providing redundant information, as is described in the next section.

The orientation of each connection is shown as a +1 (forward orientation) or −1 (negative orientation). In one aspect, as each connection has a same absolute value, each connection can be considered to have a same strength, or effectively relative strength is not considered. In another aspect, since there is no redundant information, strengths of the connections can be considered irrelevant, at least as long as each strength is above a threshold for embodiments that use such a threshold. However, strength scores could be used for other purposes, e.g., for clinical implications.

FIG. 5B shows the resulting haplotypes for the first region specified by the set 500 of sets. Het 510 has alleles C and T. Allele C is arbitrarily put on haplotype 1 and T is put on haplotype 2. The alleles of the other hets are then placed on haplotypes 1 or 2 based on the orientations. The connection between het 510 and het 520 is of forward orientation, so C of het 520 is on the same haplotype as C of het 510, which is haplotype 1. As a corollary, G of het 520 is on haplotype 2, since T of het 510 is on haplotype 2.

The orientation of the connection between het 520 and het 530 is a reverse orientation, and thus allele T of het 530 is on a same haplotype (haplotype 1) as het C of het 520. The orientation of the connection between het 530 and het 540 is also a reverse orientation, and thus allele A of het 540 is on a same haplotype as het T of het 530. This operation of the orientations means that A of het 540 is on a same haplotype as C of het 520, due to the two reverse orientations. Haplotype 1 is finished with allele G of het 550 as the orientation of the connection of het 540 to 550 is forward.

In one embodiment, the genomic information between the hets can be determined from the sequencing information of the corresponding reads and/or from one or more reference genomes. In one implementation, the genomic information between two hets can be taken as equal to the reference genome for both haplotypes, e.g., the sample can be considered to be homozygous at the loci between two sequential hets. For example, an assembler for a diploid genome can be considered to result in either heterozygous, indels, block substitutions, homozygous, hemizygous, or nocalls (indeterminate). In one aspect, all except homozygous can be captured as some kind of variation (and thus subsumed as a candidate het), and can enter the phasing process. If homozygous, then the exact stretch of homozygous calls between sequential hets can be copied for each of the haplotypes. In another implementation, the genomic information between two hets could be dependent on which alleles are at two hets, i.e., some sort of variation exists between the two hets. For example, if C at het 520 and T at het 530 are on the same haplotype, then the genomic information between the two hets can be selected as one sequence; but if instead C at het 520 and A at het 530 are on the same haplotype, then a different sequence can be chosen as being between the two hets.

Het 560 is not part of set 500 because het 560 does not have a connection to any of the hets in set 500. Thus, there is no information about which haplotype allele C or T is on. Other embodiments related to universal phasing. Note that having no connection does not necessarily mean that there were no data points suggesting a connection of one of hets 510-550 and het 560, but that the data was not statistically significant enough to make such a determination.

IV. Contig Phasing with Redundant Information

As mentioned above, the connections among hets can include redundant information. For example, a first heterozygous locus of a first set can be connected to at least two or at least five or at least ten other heterozygous loci that are both on a first side of the first heterozygous locus. As an illustration, het 510 could be connected to het 520 and to het 530. Thus, there is redundant information for connections that involve het 520 on the right side of het 520. Such redundant information can be useful when an orientation of a connection was determined incorrectly, e.g., in step 440 of method 400.

Figure 6:
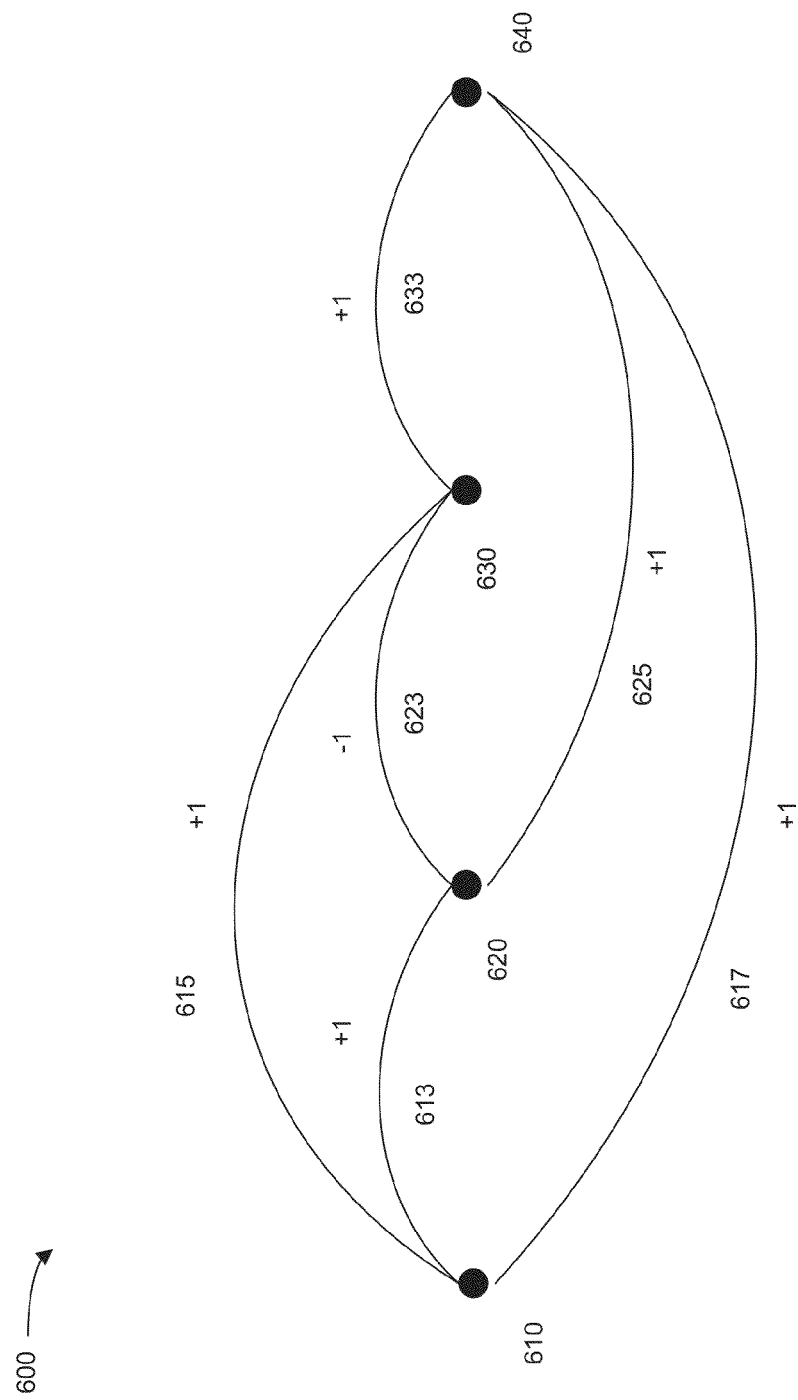
FIG. 6 shows a set 600 of hets with redundant connection information according to embodiments of the present invention.

FIG. 6 shows a set 600 of hets with redundant connection information according to embodiments of the present invention. The set 600 is shown to include hets 610-640. Each connection is shown with a line connecting the hets. In this example, each het is connected to each other het in the set. The orientation of each connection is shown as a +1 (forward orientation) or a −1 (reverse orientation).

The connection 623 between hets 620 and 630 shows a reverse orientation, which conflicts with the connection 625 between hets 620 and 640 and/or the connection 633 between hets 630 and 640. For example, if the orientations of connections 623 and 633 are indeed +1 and −1, then the orientation of connection 625 would be −1, but it is not. If these were the only three data points, then one would not know which orientation was incorrectly determined. Note that if different relative strengths were determined (discussed in the following section), it could be possible to determine the connection that is likely incorrect.

The connections 615 and 617 can provide additional information to resolve the conflict. Since connection 615 has a +1 orientation, then one of connections 613, 623, and 615 is in error. Since connection 623 shows up as a possible error in both groups, connection 623 can be identified as being more likely in error than any of the other connection. The connection 617 also has a +1 orientation, which confirms that connection 623 is in error, and should have an orientation of +1. If the only orientation information was for connections 613, 623, and 633, then the haplotypes would be determined incorrectly. Thus, the redundant information can provide increased accuracy.

Accordingly, in one embodiment, a conflict can be identified among the determined orientations of two connections involving a same het. Which of the two conflicting orientations is most consistent with the determined orientations of other connections can be determined. For example, each time a conflict is identified amount a group of connections, each connections in the group can have a counter incremented. In the above example, connection 623 would be incremented when a conflict is found with the group of 613, 623, and 615 and with the group of 623, 633, and 625. In one embodiment, greater than 5% of the connections are determined to have the wrong orientation (i.e. 2-allele haplotype above the significance thresholds is incorrect).

Besides a conflict, redundant information can fill in for missing information. For example, assume that information about a connection 633 did not exist, and thus a connection was not found between het 630 and het 640. This missing information (e.g. 10%, 30%, or 50% of tested connections) could simply occur as a result of a statistical aberration, noise, or other reason, such as not enough sequencing data was received. However, since connections 617 and 625 exist, it can be possible to determine haplotypes involving hets 630 and 640, although information about a direct connection between them does not exist.

V. Contig Phasing Using Strength Values

As mentioned above, determining a strength of a connection can provide an ability to apply more redundant information and obtain even grater accuracy. In one aspect, a strength can provide a measure of confidence that a particular orientation has been determined accurately. For example, a zero strength can mean that there is no connection between two hets, and thus no confidence in what orientation might exist between the alleles at the hets. A small strength can indicate that there is some evidence that a particular orientation of a connection is more likely than another orientation, but not too much more likely. Thus, if the connection conflicts with other connections, then the connection with the least confidence can be removed without resorting to analyze a lot of other connections.

A. Sequence Information for Strength Values

In one embodiment, the determination of a strength of a connection is determined by tracking data that suggests alleles at two candidate hets were on a same fragment of DNA or RNA. If the two alleles are considered to be on the same fragment, then that data point would suggest that the two alleles are connected and are on a same haplotype. In one embodiment, more direct knowledge of the two alleles being on a same fragment can be used (e.g. with explicit mate pairs), but such information may provide few data points. In another embodiment, an inference can be made that two alleles were on an original larger fragment that had since been broken up into smaller fragments, which are then sequenced wholly or partially (e.g. paired-end sequencing). In one implementation, the inference can be made using long fragment read (LFR) techniques as described in U.S. Pat. No. 7,709,197, entitled "Nucleic Acid Analysis By Random Mixtures Of Non-Overlapping Fragments" filed Jun. 13, 2006, and U.S. patent application Ser. No. 12/816,365, entitled "Methods And Compositions For Long Fragment Read Sequencing" filed Jun. 15, 2010, the contents of which is incorporated by reference.

In sequencing a fragment (e.g. a DMB), the two ends of the fragment can be sequenced (or possibly the whole fragment, although that is more costly). The two sequenced ends are referred to as arm reads. The locations of these arm reads in the genome can be identified, e.g., by comparing to one or more reference genomes. If the two arm reads from a same fragment are found to cover respective locations of candidate hets, then the sequences of the two arm reads can indicate how the two hets might be connected (i.e. an orientation of the connection between the hets). For example, if one arm read shows a C at a het and the other arm read shows a C at the other het, then a counter can be incremented. It is also possible that a single arm read could cover two hets. If more than one fragment has arm reads that cover these two hets, the total information can be used to determine a connection strength between the two hets. In one implementation, the length of the fragments can be varied in order to identify connections between pairs of hets of various spacing between the hets.

In one embodiment, as described below, counters of the different combinations of alleles for the two hets can form a connectivity matrix, with the counters being different matrix elements. However, the number of times that two arm reads of a fragment cover two hets can be quite small, thereby not providing much connection information. For example, if only one data point is obtained for a possible connection between two hets, that data point could be the result of a sequencing error or other error in preparation, and thus may not be reliable since the event has occurred only once. In another implementation, the length of the fragments can be varied (i.e. the fragments whose ends are sequenced, which equates to varying the length of gaps between the arm reads) in order to identify connections between pairs of hets of various spacing between the hets.

In an embodiment using LFR techniques, an origin of each sequenced fragment is tracked. For example, a solution including one or more samples of nucleic acid molecules of an organism can be created. In the solution, the nucleic acid molecules tend to be much longer than after the solution is dispensed (e.g. from a pipette) as an aliquot into wells for preparation for sequencing. These very long fragments can be about 100 kb to 1 mb in length.

The act of dispensing typically breaks up the nucleic acid molecules, e.g., as they move through the tip of the pipette. The nucleic acid molecules before dispensing are termed very long fragments, and the nucleic acid molecules after dispensing are termed long fragments. The long fragments in a well (or other container holding a single aliquot) are about 5 Kb to 50 Kb in length (or up to a few 100 s of Kb).

The long fragments can be fragmented, e.g. using enzymatic fragmentation, multiple displacement amplification (MDA) with random primers, and/or physically fragmented (e.g. using sonic fragmentation). Short fragments (also simply called fragments) result from the fragmentation of the long fragments. As part of an enzymatic process or as an additional step, the resulting short fragments may be amplified. In various embodiments, the resulting short fragments can be about 100-10,000 bases, or a more narrow range of 200 bases to 5,000 bases, and may be 500 bases on average. Thus, the fragments that are actually sequenced (partially or entirely) are smaller than the long fragment and the very long fragments. However, sequencing the smaller fragments can provide advantages.

Certain embodiments can track the aliquot (or well) from which a sequenced fragment was obtained, thereby recapturing information about the longer fragments that existed in the solution. This information about the longer fragments can provide more connection information about the haplotypes of the respective chromosomes. In one embodiment, the solution can be relatively diluted with respect to the nucleic acid molecules (e.g. as few as about 10 cells may be in the solution). This dilution can provide an aliquot containing around 10% of the genome when the solution is dispensed from a pipette. Given that the long fragments are randomly distributed throughout the solution, the original fragments of an aliquot are not likely to be from overlapping regions of the genome, nor be close to each other, and to be from different copies of the a chromosome. Accordingly, if arm reads from any two fragments in a same aliquot are close in genomic location, it can be assumed that they originated from a same original fragment in the solution. Thus, the arm reads do not have to be of a same fragment, but can be from any two fragments that are from the same aliquot. Such tracking provides more connection information. Two reads can be said to be correlated if they are from a same fragment (e.g. from a same read or from a pair of mated reads) or from a same aliquot.

Any of these embodiments for obtaining sequencing information can be used with the analysis methods mentioned herein. Some embodiments can use multiple methods of obtaining sequencing information. For example, the arm reads of a same fragment can be used, as well as LFR techniques that use arm reads for any fragment of a same aliquot. In one embodiment, arm reads of a same fragment could be given a higher weight than when the arm reads are from different fragments (but from a same aliquot). In one aspect, embodiments using LFR techniques can benefit from the use of connection strengths to correct inaccuracies due to assumptions of the LFR techniques.

B. Determining Strength Values

In one embodiment, identifying a connection and the corresponding strength can use a connectivity matrix. A connectivity matrix can be created from a variety of different sequencing information, e.g., as is described above. A connectivity matrix can allow a tracking of data points about which alleles from different loci originated from a same fragment.

Figures 7A, 7B, 7C:
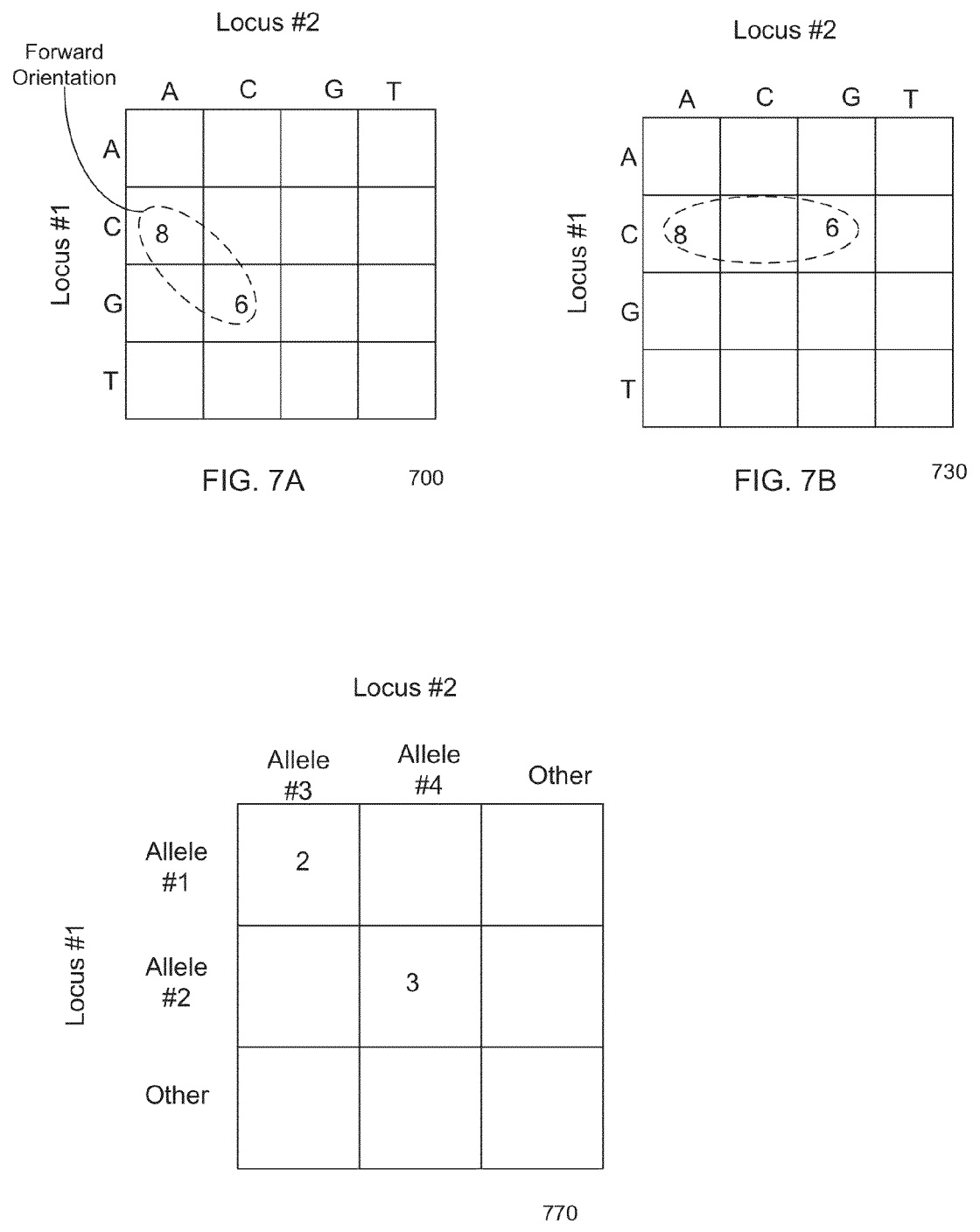

FIG. 7A shows a connectivity matrix 700 for a locus #1 and a locus #2 according to embodiments of the present invention. Each row has a respective nucleotide for locus #1, and each column has a respective nucleotide for locus #2. In one embodiment, each matrix element corresponds to an existence of a particular nucleotide on locus#1 being identified as being from a same fragment as a particular nucleotide on locus#2, e.g., by being from a same read, from mated reads, or from reads of a same aliquot. Such a matrix element can convey whether the alleles are correlated.

In an example using LFR techniques, the matrix element of (C,A) can correspond to a number of times that C showed up at locus#1 and A showed up at locus#2 for any of the fragments from a same aliquot. The value of "8" can result from a sum of all such shared counts across all aliquots. In one implementation, the count for a particular aliquot is the smaller of the counts for the respective nucleotides. For example, if C shows up at locus#1 3 times for aliquot#1, and C shows up at locus#2 2 times for aliquot#1, then the value of 2 is added to the (C,A) matrix element.

In one embodiment, a strength value for a particular orientation of a connection can be determined by the number in the relevant matrix elements. For example, the relevant matrix elements in connectivity matrix 700 for a forward orientation are shown as (C,A) and (G,C), where the het of locus#1 is C/G and the het of locus#2 is A/C. The higher the values in these matrix elements, the higher the strength score for this orientation. The relevant matrix elements for the reverse orientation would be (C,C) and (G,A). For a particular orientation, the strength can also be based on the values in the other matrix elements (e.g., the matrix elements corresponding to the other orientation). For example, the strength score can decrease with higher values in the other matrix elements.

A connectivity matrix could be made to have three dimensions, e.g., by adding in a third locus. Such a connectivity matrix would describe connections among three loci.

A connectivity matrix can also be used to determine whether a candidate het is indeed a het. FIG. 7B shows a connectivity matrix 730 where locus #1 is likely homozygous for the nucleotide C according to embodiments of the present invention. As shown, the nucleotide C shows up with two different nucleotides of locus#2. Such a behavior of appreciable values in a single row or a single column suggest that the respective locus is homozygous. In another embodiment, one could just look at the data for a particular locus to determine a percentage of different nucleotides.

Besides different SNPs, a locus can have insertions and deletions (collectively referred to as indels). A connectivity matrix from above can be generalized to handle any type of allele. FIG. 7C shows a connectivity matrix 770 for determining a connection of alleles at locus #1 and locus #2 according to embodiments of the present invention. In the example of connectivity matrix 770, locus#1 is potentially heterozygous for alleles #1 and #2, and locus 2 is potentially heterozygous for alleles #3 and #4. The connectivity matrix can be used to test hypotheses of these two loci being heterozygous and being connected, with a particular orientation. The "Other" categories can help determine a strength of the connection of particular values. The alleles on either locus could be the same or different. The other category could also be expanded to identify other connections besides just two alleles of each locus. For example, each locus could have 3 or more alleles. And, each locus could have a different number of alleles.

In one embodiment, the matrix element could be modified based on the reference genome. For example, the values of relevant matrix elements could be increased based on a general likelihood of two hets being connected in a particular way (i.e. the orientation is generally the same). Thus, information besides the specific sequencing information could be used (e.g., population genetics).

In some embodiments, if there is not a clear connection, e.g., every matrix element has the same value, then it can be determined that the sequencing information does not support a determination that a connection exists between the hets. In one embodiment, there could be a threshold for the individual matrix elements for a connection to be determined (e.g., greater than 1 or 2), or a threshold for a total score derived from all of the matrix elements. Such thresholds could be based on normalized values or absolute values. In various implementations, there could be more than one threshold cutoff. In an embodiment, only one orientation of a connection is determined between hets.

In one embodiment, the values for the matrix elements can be real numbers. In one implementation, some data can be deemed more reliable than other data, and thus a count could be reduced or increased as appropriate, e.g., by scaling (multiplying, dividing, or other function) by a confidence value.

The scaling can depend on the type of correlation between the two alleles. For example, the confidence value can depend on an estimated accuracy of the sequences read, whether a count of a matrix element involve allele reads from a same arm read, allele reads from a mated pair of reads, and whether the arm reads are from non-mated arm reads (e.g., arms of different fragments) but a same aliquot.

Figure 8:
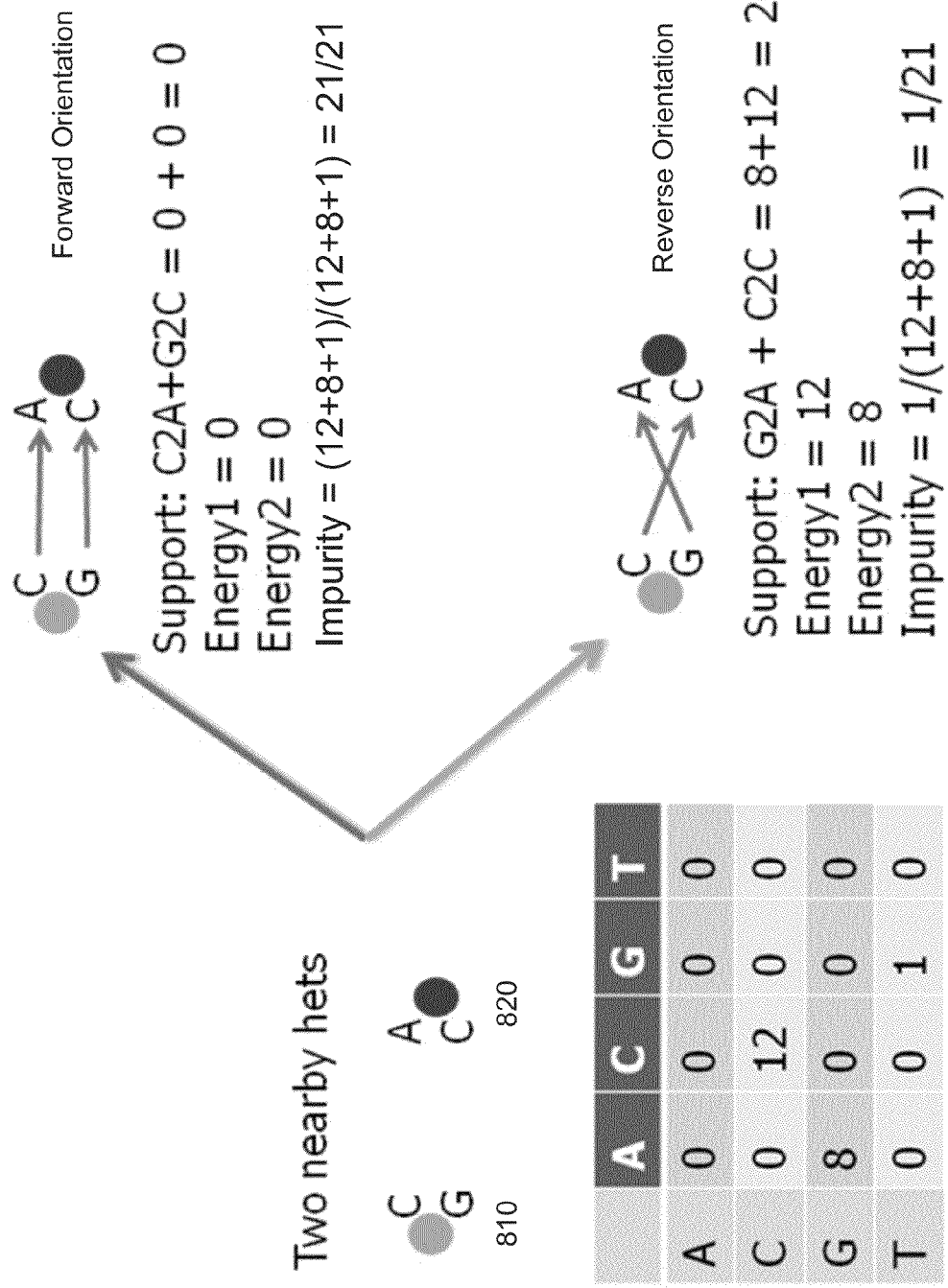
FIG. 8 shows an example of using a connectivity matrix 800 to determine a connection between two candidate hets and/or determine an orientation of a connection according to embodiments of the present invention.

FIG. 8 shows an example of using a connectivity matrix 800 to determine a connection between two candidate hets and/or determine an orientation of a connection according to embodiments of the present invention. Connectivity matrix 800 shows the data points for the instances of reads covering the two loci of the candidate hets. As shown, the matrix elements (G,A) and (C,C) are much higher than the other matrix elements. Accordingly, it can be determined that the two hets have a reverse orientation for their connection. Various embodiments can be used to determine such an orientation.

In some embodiments, two or more hypotheses are formed for the connection between the hets. If the sequenced data predominantly shows two alleles at each het, then the two hypotheses can be a forward or reverse orientation (as described above). If it is not clear which two alleles might be at a particular het (e.g., relatively similar amount of three alleles, or one higher and two with similar amount), then more than two hypotheses could be tested.

In one embodiment, to test a hypothesis, the two matrix elements (also called energies) that define the orientation between the alleles of the possible connection are identified. These matrix elements are examples of a positive contributions in that they contribute to a greater confidence of a hypothesis. As noted above, the matrix elements could be real values as well. For example, for the forward orientation between alleles C/G of het 810 and alleles A/C of het 820, the two matrix elements are (C,A) and (G,C). These energy values are both zero, which is an indication that no data points suggest that C on het 810 and A on het 820, or G on het 810 and C on het 820, showed up on a same fragment. In some implementations, the energy values could be a function of the matrix elements (e.g. respective scaling factors or the same scaling factor could be applied to the matrix elements).

In one embodiment, an impurity can be calculated, which is an example of a negative contribution to a strength. A negative contribution denotes a negative contribution to confidence, but can have any sign depending on how a strength is formulated (e.g. more negative values signifying greater confidence or an inverse formulation). The impurity can compare the energies of a particular hypothesis with the values in the other matrix elements. In one aspect, the impurity can convey that another hypothesis has similar energies, and this either hypothesis may not be very strong, and thus have reduced strength scores. In one embodiment, the impurity is a function (e.g., involving a simple sum or weighted sum) of the other matrix elements. A sum is of the other matrix elements is 21. In one implementation, the impurity can provided as a sum of the matrix elements not involved in the hypothesis (21 in this case) divided by a sum of all the matrix elements. In this case, the two values are the same, and the impurity becomes 1 (or 100%), thus confirming that this hypothesis is not valid.

The other hypothesis of a reverse orientation shows the energy values of 8 and 12 (examples of a positive contribution to a strength), and an impurity of 1, which can be represented as 1/21 (examples of a negative contribution to a strength). In one embodiment, heuristics can be used to analyze these values and determine that it is a winning hypothesis, which could provide that a simple connection exists (without calculating a specific strength score). Such a determination can be used with embodiments herein that do not use relative strengths between orientations of different connections. In other embodiments, the matrix elements and/or energies (e.g., if different) can be used to calculate a strength score.

Various embodiments can use this information in different ways. For example, one embodiment could use a support value (e.g., a sum of the relevant energies) and the impurity value. These two values could be input into a function (e.g. a fuzzy inference system) that outputs a strength score. As another example, the three values of energy1, energy 2, and the impurity could be input into a function. Separating the two energies could find instances where one energy is much higher than another energy, which could suggest a lower strength since the other haplotype was not seen very often, even though the total support is high. Other embodiments can use the values of all the matrix elements and input those into a function, or breakdown these 16 variables into any number of fewer variables from which to calculate the strength score. Additionally, the impurity value could be broken down into one part involving a competing orientation (i.e. the energies of another orientation) and the other matrix elements, which could be referred to as noise. Such calculations of strength can be used to obtain a haplotype.

C. Using Strength Values

Figure 9:
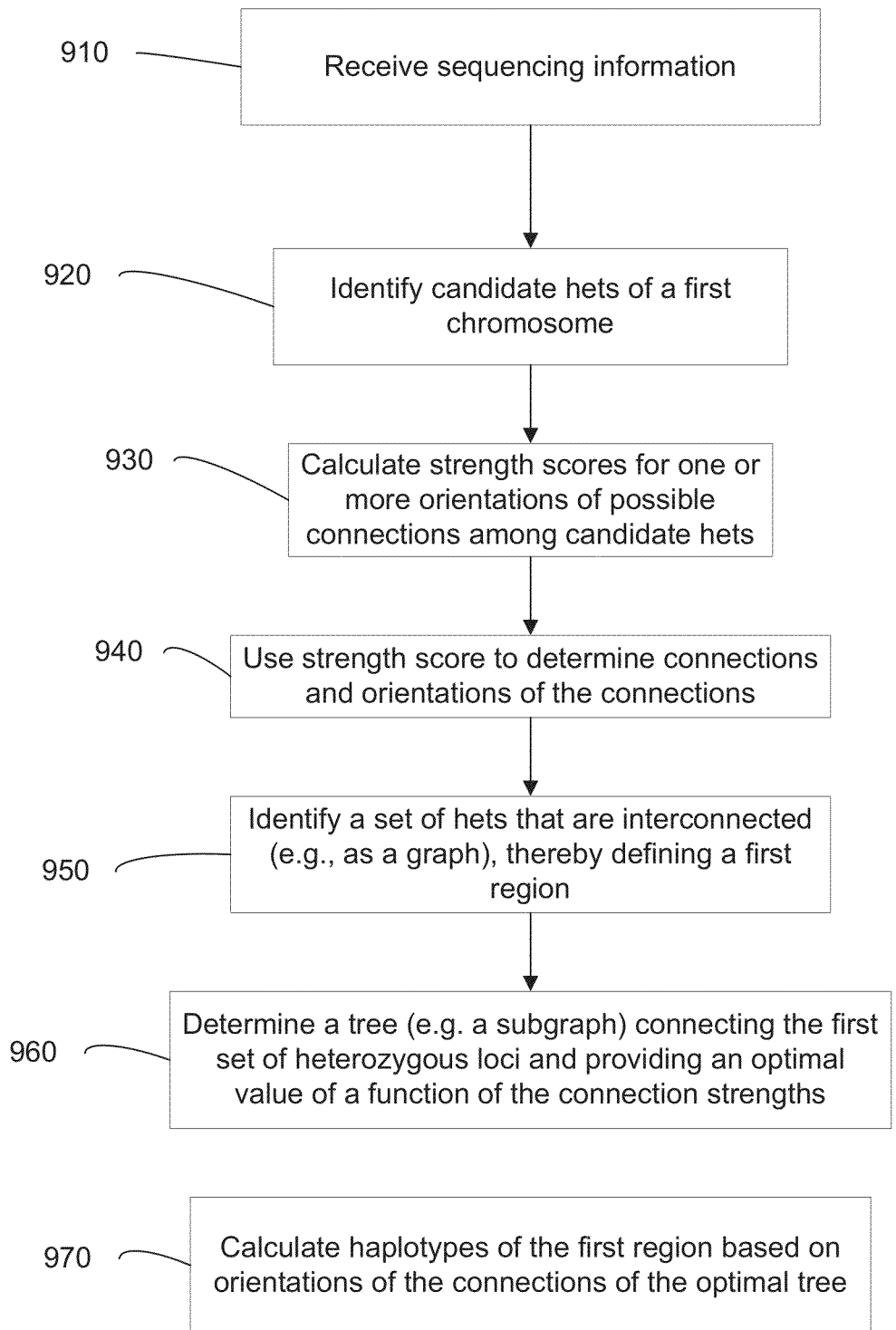
FIG. 9 is a flowchart of a method 900 using strength scores of connections to determine at least part of a genome of an organism from one or more samples according to embodiments of the present invention.

FIG. 9 is a flowchart of a method 900 using strength scores of connections to determine at least part of a genome of an organism from one or more samples according to embodiments of the present invention. In one embodiment, method 900 can be used for step 130 of method 100. Method 900 can also incorporate various aspects of method 400.

In step 910, sequencing information of a plurality of the nucleic acid molecules in the one or more samples is received. The sequencing information can have many forms, e.g., as is described herein.

In step 920, a plurality of candidate hets are identified for a first chromosome. In one embodiment, a candidate het is a locus identified as having or potentially having two or more different alleles. Candidate hets can be identified as described herein, e.g., from the reference genome and/or the sequencing information.

In step 930, strength scores for one or more orientations of possible connections among candidate hets are calculated. In one embodiment, the strength scores are calculated for respective pairs of candidate hets. As mentioned above, a neighbor cutoff can be used so that strength s scores are only calculated for hets that are close enough to each other.

The strength score can be determined in various ways, e.g., according to embodiments mentioned above. In one aspect, only one score for a possible connection may need to be calculated. For example, if a first strength score is above a threshold, then it can be assumed that the orientation (hypothesis) was correct. More than two scores could also be calculated if more than two hypotheses are tested (e.g., if a candidate het might have more than two alleles).

In step 940, the strength score is used to determine connections and orientations of the connections. For example, the strength score can be used to determine the orientation of a particular connection, e.g., the orientation can correspond to the hypothesis with the highest score (the winning hypothesis). In one embodiment, the strength scores for a particular pair of candidate hets can be used to determine whether a connection actually exists (e.g., whether the data is clear enough to ascertain with sufficient accuracy which allele of one het is on a same haplotype as an allele on the other het). For example, the highest strength score for the hypotheses for a pair of hets can be compared to a threshold, and if the highest strength score is below the threshold then the pair of hets can be considered as not being connected. Even though, the highest strength score may be above the threshold, the determined orientation can still be incorrect, e.g., as may be determined through redundant information. In another embodiment, the strength score can verify whether the candidate het is indeed a het. In one aspect, only candidate hets that are determined to have a connection are considered hets.

Regardless of the type of sequencing information used and how the data points are used to determine whether a connection exists, embodiments can consider a compromise between more data and an inaccuracy of this additional data. For example, in order to get more connections (which can be useful in determining haplotypes), then one might accept a connection with a low strength (e.g. only a few pieces of data). Since assays are not perfect, there can be errors, particularly if only a few pieces of data are obtained. But, a desire to minimize possible errors can be balanced with a desire to have more connections for use in determining haplotypes.

In step 950, a first set of at least three interconnected heterozygous loci that are interconnected are identified. As with step 450 of method 400, the connections to each other can be direct (e.g., via a single pair-wise connection) or via one or more intermediate connections. Thus, one could start from any heterozygous loci of the set and reach each other heterozygous loci of the set along connections. This first set of heterozygous loci can define a first region of the first chromosome.

In step 960, a tree that connects the first set of heterozygous loci and that provides an optimal value of a function of the connection strengths is determined. A tree is a collection of connections in which any two hets are connected by exactly one simple path (a set of connections between the two hets). Given that the tree connects the first set of hets, the tree can be considered to span the first set. The optimal tree can be selected from among a plurality of different trees that connect the hets of the first set. In one embodiment, the different trees can be considered a graph, and each of the individual trees to be a subgraph. In one aspect, the strengths and/or orientations can be used to resolve conflicting redundant information.

In one embodiment, there can be more than one optimal tree. For example, multiple trees can be optimal and any one of them can be selected. Thus, the optimality can be that the set of trees are optimal over another set of trees. In one implementation, the function is a sum of the strengths. In another implementation, the optimal value can be the highest value among a plurality of trees, or one tree from a group of trees whose values satisfy a criteria. For example, the group can be made of trees that are consistent with each other (e.g. no conflicts) and have function values that are higher that than the inconsistent tree with the highest function value.

In step 970, the haplotypes of the first region are calculated based on orientations of the connections of the optimal tree. Once an optimal tree is selected, the orientations of the connections of the optimal tree can be used in a similar way as described in step 460 of method 400 to determine the haplotypes.

Phasing can be important for accuracy due to inaccuracies and/or deficiencies in the sequencing information. As mentioned above, the connection information is not typically definitive, and the connection information may not be consistent. There may be a conflict between the connection information.

Figure 10A:
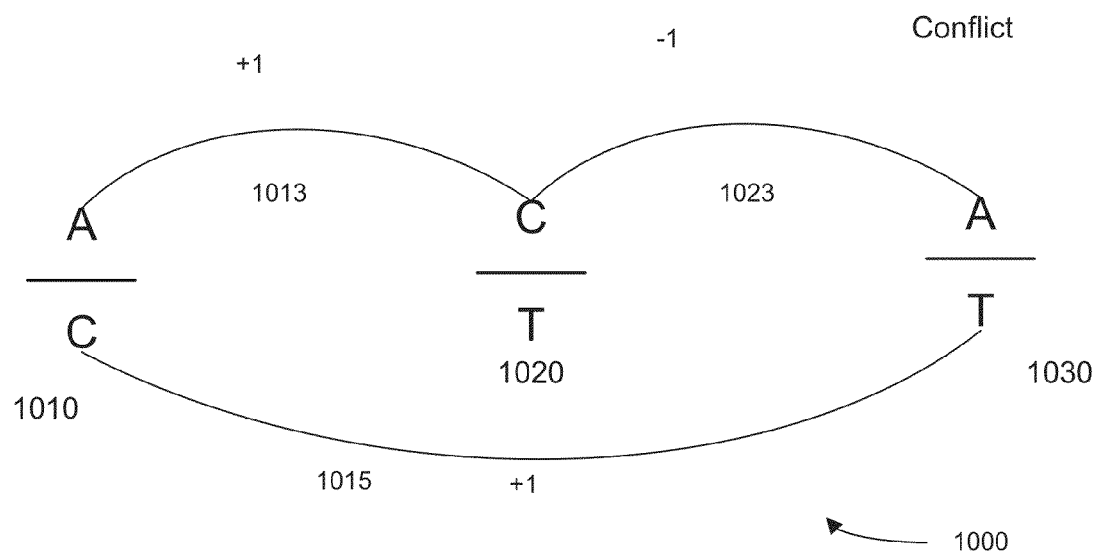
FIG. 10A shows a graph 1000 illustrating a conflict among the orientations of the connections of a set of 3 hets according to embodiments of the present invention.

FIG. 10A shows a graph 1000 illustrating a conflict among the orientations of the connections of a set of 3 hets according to embodiments of the present invention. The three hets are het 1010 with A/C, het 1020 with C/T, and het 1030 with A/T. Each het is shown connected with every other het in the set. The orientations of the connections are shown as "+1" and "−1". Relative strength information is not provided.

As one can see, there is a conflict among the connections. The connection information suggests that A-1 and C-2 are on the same haplotype (connection 1013), and A-1 and A-3 are on the same haplotype (connection 1015). Thus, one would normally presume that one chromosome copy has A,C,T at the three hets. But, the connection information also suggests that C-2 and T-3 are on the same haplotype (connection 1023), which contradicts the other information. However, since no strength information is conveyed (i.e. all have the same absolute value), one cannot determine which connection is likely to be inaccurate.

Figure 10B:
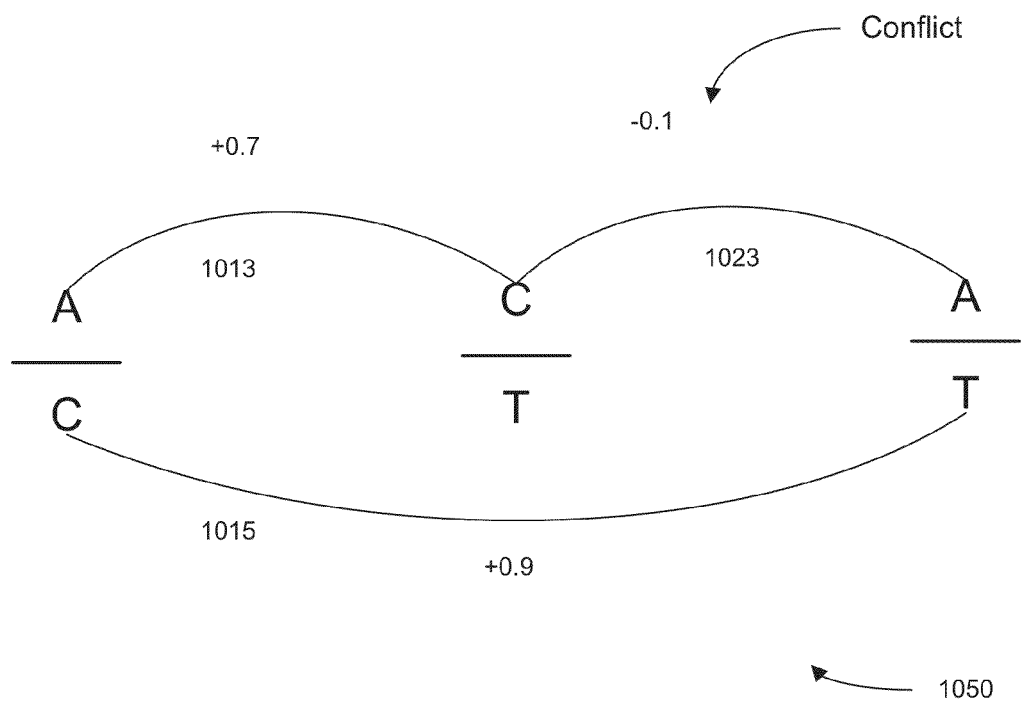
FIG. 10B shows a graph 1050 showing connection strengths and illustrating a conflict among the set of 3 hets according to embodiments of the present invention.

FIG. 10B shows a graph 1050 showing connection strengths and illustrating a conflict among the set of 3 hets according to embodiments of the present invention. Graph 1050 shows connection strengths for each of the connections in graph 1000. Note that the orientations are still shown with a "+" or a "−" sign before the strength score. In one embodiment, the strengths are provided as a value between 0 and a maximum value (e.g. 1), and can be integers or real values (if integer, the maximum should be greater than 1). As shown, connection 1013 has a strength of 0.7, connection 1015 has a strength of 0.9, and connection 1023 has a strength of 0.1. Given that connection 1023 has a low strength, one can see that it is the connection that is likely inaccurate, and therefore in conflict.

Figure 11:
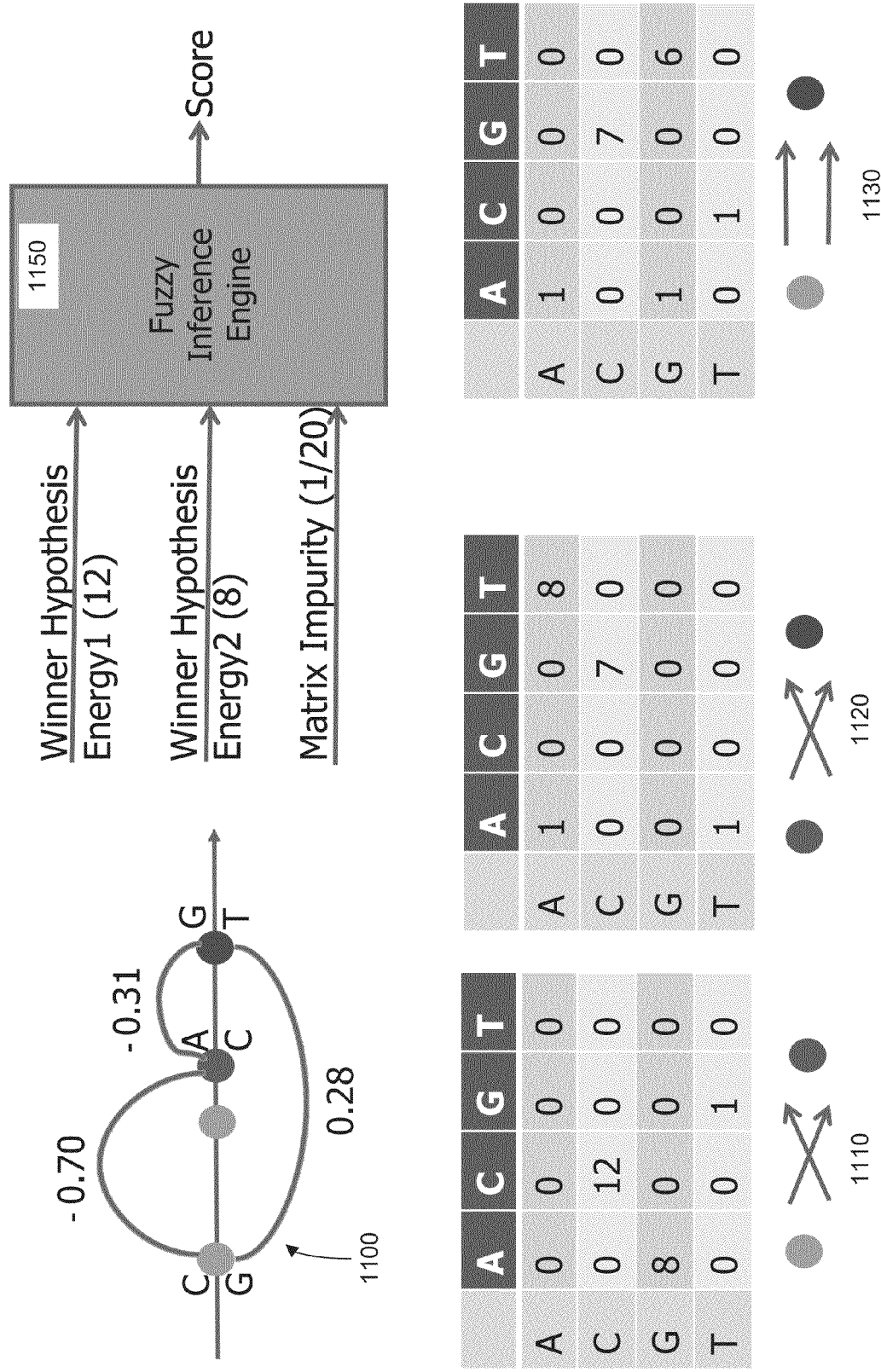
FIG. 11 shows a diagram illustrating a graph of three hets and the corresponding connectivity matrices for the connections among the hets according to embodiments of the present invention.

FIG. 11 shows a diagram illustrating a graph of three hets and the corresponding connectivity matrices for the connections among the hets according to embodiments of the present invention. Connectivity matrix shows connection information between the first het C/G and the second het A/C. The energies are 8 and 12, and the impurity is measured as a sum of the other matrix elements divided by a sum of the elements. These three values can be input into a fuzzy inference engine 1150 to obtain the strength score. In this example, the connectivity matrix 1110 has a strength score of 0.7 for a reverse orientation, and thus is shown with a −0.7 in the graph 1100. In one embodiment, a distance between the two hets could also be used, e.g., input into the fuzzy inference engine.

Connectivity matrix 1120 results in a strength of 0.31 for the reverse orientation. In comparison to connectivity matrix 1110, one can see that the impurity is larger and one of the energies is lower, thereby providing a lower strength. Connectivity matrix 1130 results in a strength of 0.28 for the forward orientation. The orientations of graph 1100 are consistent.

D. Example of Determining the Optimal Tree

In samples where there is on average a het every 1500-2000 bases, then every 50 kb, there are around 50 hets. Certain regions can be even more dense, e.g., 400 hets in region of interest (e.g. a 50 kb region). Each het could connect with each other het in the region. So a set of connected hets (which may be depicted as a tree or graph) can be quite dense. In one embodiment, a minimum or maximum spanning tree method is used, e.g., according to the Kruskal Method.

Figure 12:
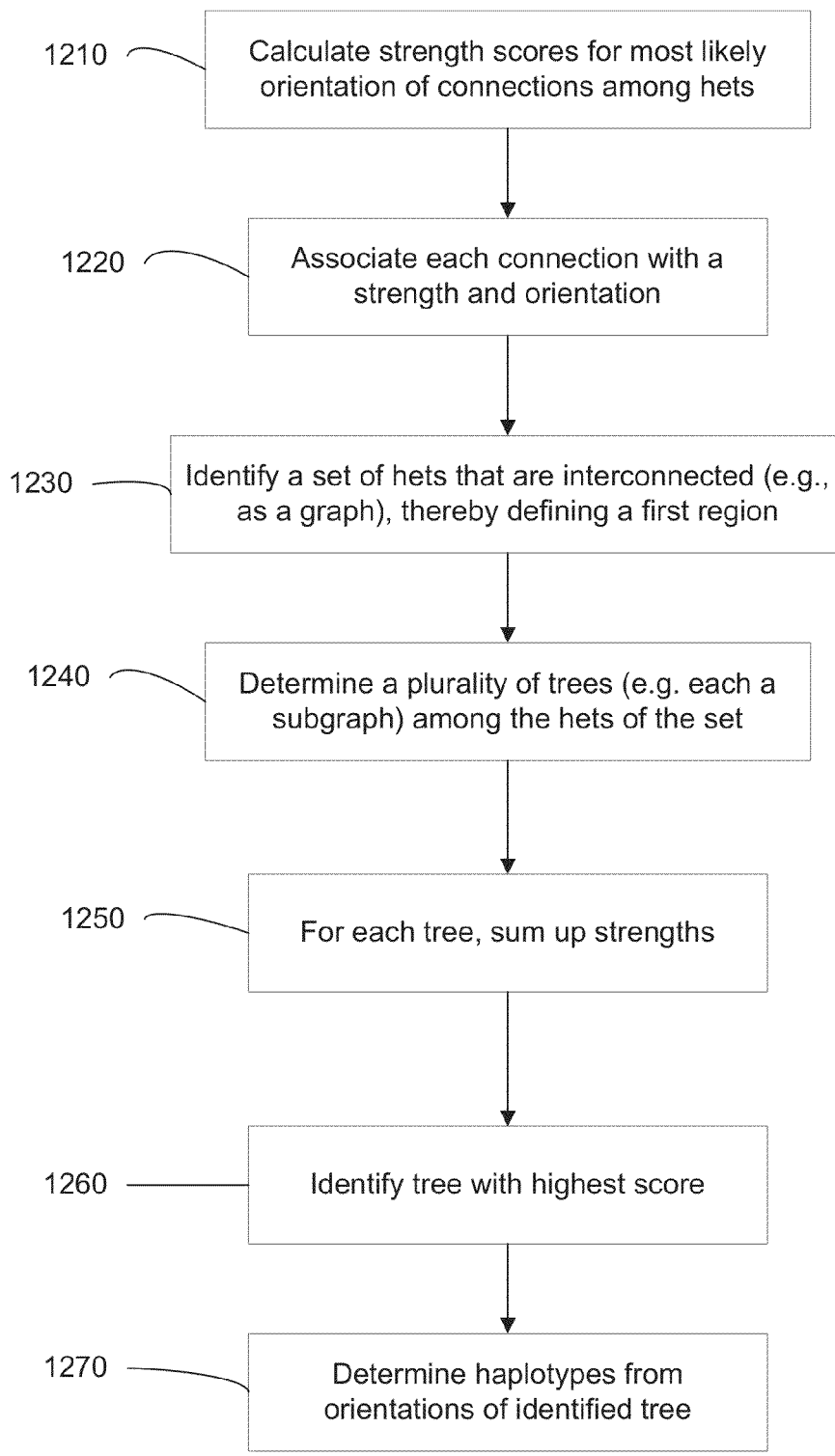
FIG. 12 is a flowchart of a method 1200 for determining an optimal set of connections among a set of hets to determine a haplotype according to embodiments of the present invention.

FIG. 12 is a flowchart of a method 1200 for determining an optimal set of connections among a set of hets to determine a haplotype according to embodiments of the present invention. In one embodiment, parts of method 1200 can be used for step 960 of method 900. Method 1200 can also incorporate various aspects of method 900.

In step 1210, strength scores can be calculated for a likely orientation of connections among hets. As mentioned above, the strength scores can be used to determine the likely orientation, whether a connection exits, and whether a candidate het is a het. The strength scores can take many forms, e.g., values between 0 and 1, integers between 1 and 10 or 1 and 100, and other suitable classifications. As an example, the orientation can be signified by a positive or negative sign of the strength value.

In step 1220, each connection is associated with a strength and orientation. The associations can be stored in various ways. For example, each connection can have a unique identifier (e.g., a number signifying a particular connection between two hets), and the strength and orientation can be associated with that identifier. As another example, a two-dimensional array can be used to store the associations. Each row of the array can correspond to a het, with the column corresponding to the other het of a particular connection, and the stored value can correspond to the strength and orientation. Such an array can be stored as a sparse matrix.

In step 1230, a set of hets are identified that are interconnected (e.g., as a graph). As with steps 450 and 950, the connections to each other can be direct (e.g., via pair-wise connection) or via one or more intermediate connections. Thus, one could take at least one path from heterozygous loci of the set and trace a path to any of the other heterozygous loci of the set along the connections. This first set of heterozygous loci can define a first region of the first chromosome.

In step 1240, a plurality of trees among the hets of the set are determined. In one embodiment, the set of trees among the hets can be considered a graph, and each of the individual trees to be a subgraph. The plurality of trees could include all of the possible trees or just a subset. The trees can be determined in various ways. For example, one het can be used as the starting point (e.g. a het at the end of the set) and connections can be used to tie in the other hets. Each time more than one option for a connection is available, an algorithm can return to that decision point to determine a new tree. It is possible that just one tree is available, and thus some of the following steps can be skipped.

In step 1250, the strength of the connections for a particular tree is summed to obtain an overall score. In a more general sense, any function could be to determine the overall score for a particular tree. For example, a function could take the inverse or reciprocal value of each strength and then sum. Which function is used can impact the application of subsequent steps. The overall scores for each of the trees is also determined.

In step 1260, the tree with an optimal score (e.g. highest score) is identified. This tree can be considered an optimal tree that provides the most likely set of connections. In other embodiments, the function for an overall score could be such that the tree with the smallest score is identified as providing the most likely set of connections. Also, as mentioned above, a group of trees can be identified, and any tree within that group can be selected. For example, assume that the trees with the five highest scores (or five more than a pre-specified threshold) are all consistent with each other, where the sixth highest score has at least one conflict with this group of trees. Then, any of the trees in the groups may be chosen.

In one embodiment, such a step of finding an optimal tree among a plurality of trees can use methods for determining a minimum or maximum spanning tree. For example, lower strength connections (edges) can be eliminated in favor of connections with a higher strength. In one aspect, a minimum/maximum spanning tree increases almost linearly with the number of loci.

In other embodiments, other optimization algorithms can be used. For example, the cost function to be minimized (or maximized) is a function of the connections of the set of hets. This cost function can be optimized with a constraint that the optimal score corresponds to a spanning subset (e.g. a graph) of the connections that do not include conflicts. In one implementation, the optimization could determine a 0 or a 1 as a multiplier for each connection (0 if the connection is not part of the answer), and thus search the space of these coefficients to minimize (or maximize) the cost function. In one aspect, the characteristic of the subset of connection forming a spanning tree can automatically result from the optimization (e.g. extra connection would be removed without a lost of the spanning characteristic).

In step 1270, the haplotypes of the first region are determined from the orientations of identified tree. For example, an aggregate orientation for multiple connections between an anchor het and second het can be used. As described above, a forward connection of a second het of A/C with an anchor het of G/T can identify A and G being on the same haplotype. In one embodiment, the sign of each connection on the path from the second het to the anchor het can be multiplied against each other to determine an aggregate orientation. The aggregate orientation can then be used just like a regular orientation to determine which haplotype the alleles of the second het are on (e.g., using a convention that the first allele of the anchor het is on the first haplotype, where the first allele can always be the one being first alphabetically). For instance, the if the second allele is connected with the anchor het through two connections (both reverse orientation) in the identified tree, then $-1*-1=1$, and thus there is a forward orientation between the second het and the anchor het.

Figure 13A:
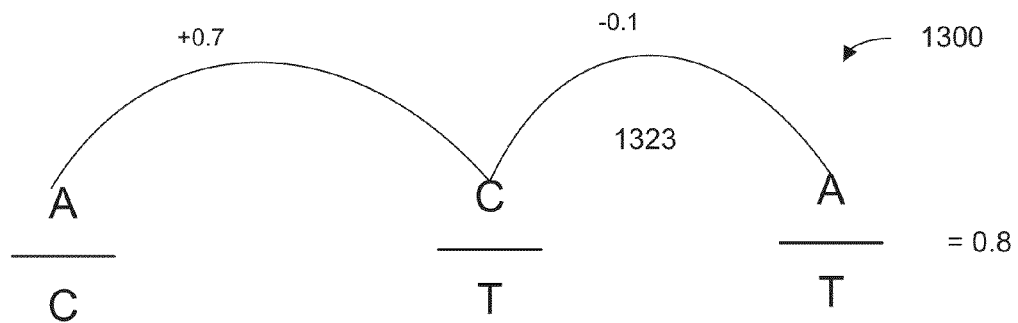
FIGS. 13A-13C show three different trees of three hets illustrating a determination of an optimal tree according to embodiments of the present invention.
Figure 13B:
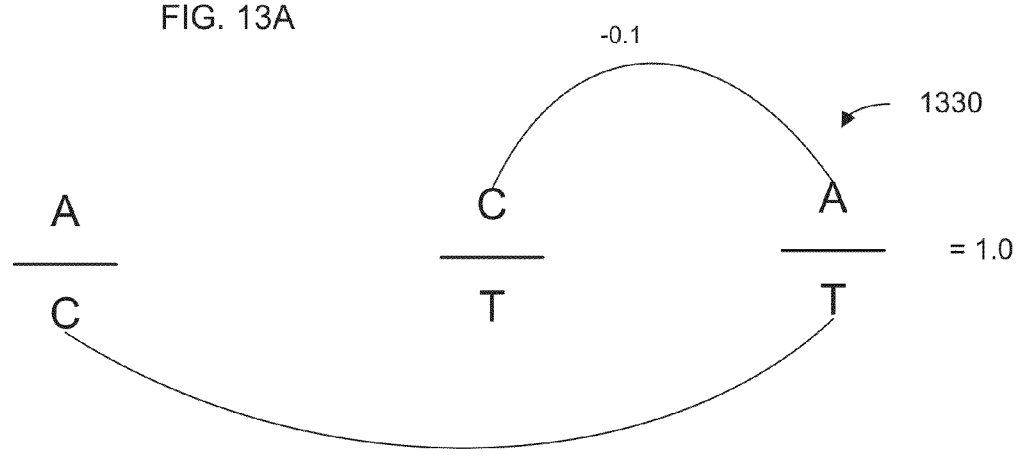
Figure 13C:
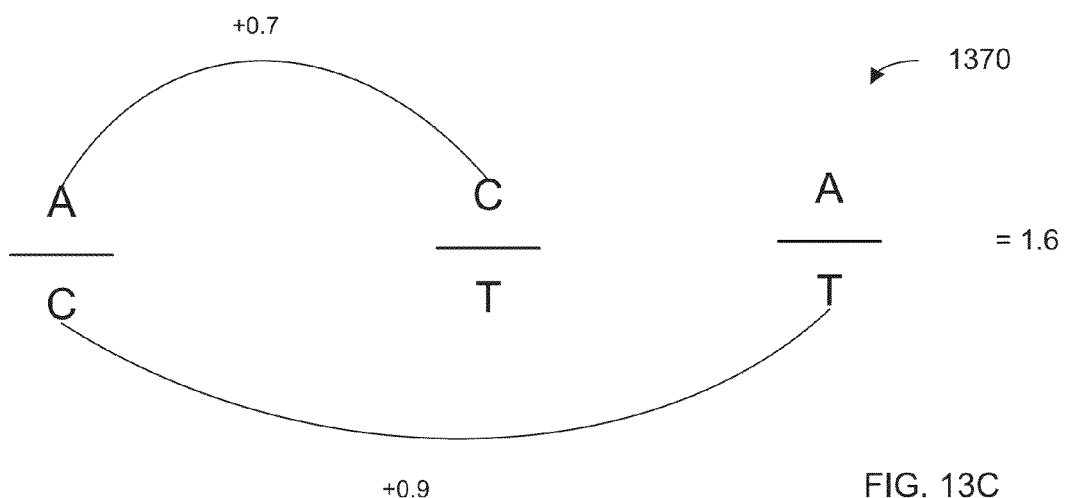

FIGS. 13A-13C show three different trees of three hets illustrating a determination of an optimal tree according to embodiments of the present invention. The trees of hets correspond to the set of hets and connection strengths of FIG. 10B. Given that there are three hets in FIG. 10B, each connected to the other two hets, there are three possible trees.

FIG. 13A shows a tree 1300 whose connections have strengths of 0.7 and 0.1, and thus the sum of strengths equals 0.8. Note that the absolute values of the numbers are used in the sums as the signs correspond to the orientations and the strengths to the absolute numbers. FIG. 13B shows a tree 1330 whose connections have strengths of 0.9 and 0.1, and thus the sum of strengths equals 1.0. FIG. 13C shows a tree 1370 whose connections have strengths of 0.7 and 0.9, and thus the sum of strengths equals 1.6. These sums can be computed as part of step 1250 of method 1200.

Accordingly, the tree 1370 of FIG. 13C is the optimal tree. Each of the other trees are also inconsistent with tree 1370 since they include the conflicting connection. The determination of tree 1370 as the optimal tree can be performed as part of step 1260 of method 1200.

Figures 14A, 14B:
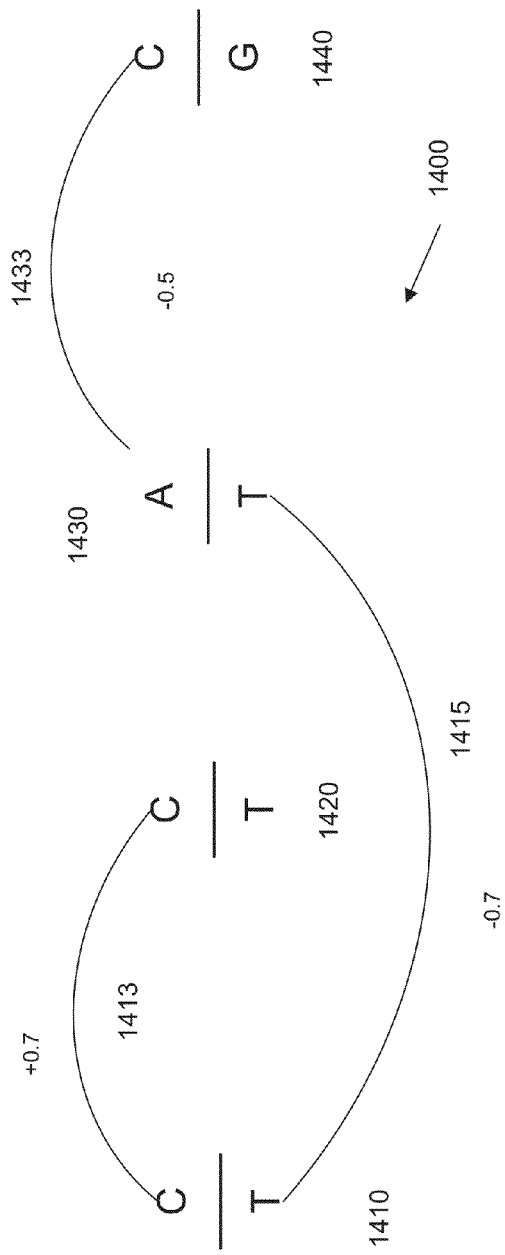
FIGS. 14A-14B shows the connection strengths and orientations of an optimal tree 1400 and the resulting haplotypes according to embodiments of the present invention.

FIGS. 14A-14B shows the connection strengths and orientations of an optimal tree 1400 and the resulting haplotypes according to embodiments of the present invention. FIG. 14A shows just the optimal tree for a set of four hets. Each het is listed alphabetically for the alleles of the respective het. For example, for the first het, C is listed before T. FIG. 14B shows the resulting haplotypes for tree 1400.

Assuming that het 1410 is the anchor het, then the forward orientation for connection 1413 provides that the C of het 1410 and C of het 1420 are on the same haplotype (which by matter of convention is labeled haplotype 1). The reverse orientation (minus sign in front of strength) of connection 1415 can provide that the alleles of het 1430 are flipped, so that T is on haplotype 1 and A is on haplotype 2. For het 1440, the path from anchor het 1410 to het 1440 involves two connections with a negative orientation. Multiplying $-0.7*-0.5$ provides a positive result, thereby providing the same result as a positive connection with anchor het 1410. Accordingly, C of het 1440 is on haplotype 1 along with C of anchor het 1410.

Figure 15A:
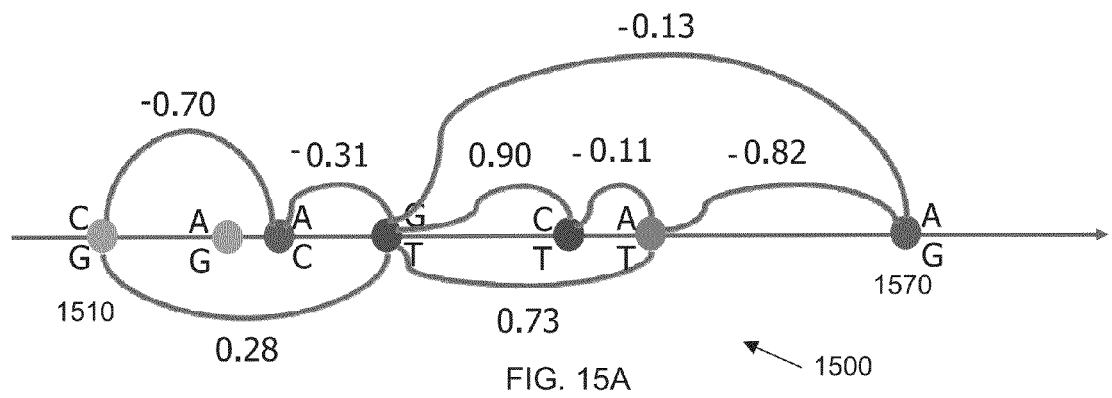
FIG. 15A shows an example of a graph 1500 for a set of connected hets according to embodiments of the present invention.

FIG. 15A shows an example of a graph 1500 for a set of connected hets according to embodiments of the present invention. The connections shown correspond to the winning hypothesis for each connection. The orientations are shown with a minus sign, and no minus sign (effectively corresponding to a positive sign). In one embodiment, the region defined by graph 1500 is between the first het 1510 and the last het 1570. The region can be used as a contiguous section in step 130 of method 100.

As one can see there is redundant connection information. For example, the connection between the first and fourth het (starting from the left) has a positive direct connection of 0.28, and intermediate connections of −0.7 and −0.31, which also provides a positive connection between the first and fourth hets. Thus, this redundant information is consistent. However, the redundant information between the fourth het and the sixth het shows a conflict. Note that the second locus (a candidate het) does not have any connections, and thus may be considered to not be a het.

Figure 15B:
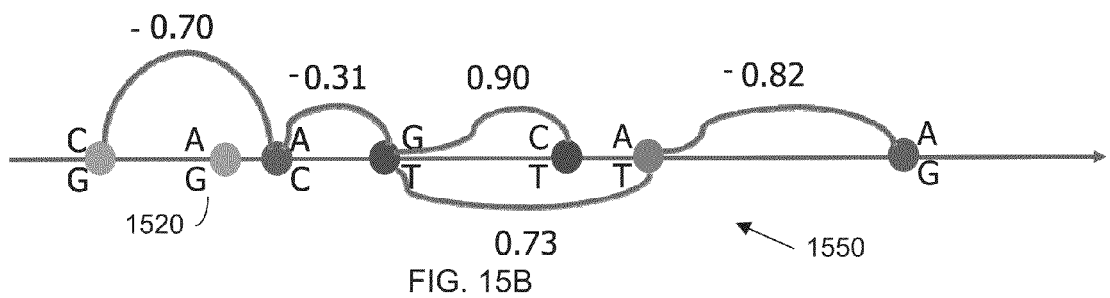
FIG. 15B shows the optimal tree 1550 of graph 1500 of FIG. 15A according to embodiments of the present invention.

FIG. 15B shows the optimal tree 1550 of graph 1500 of FIG. 15A according to embodiments of the present invention. The optimization to determine optimal tree 1550 can be done by making a minimum spanning tree (MST) from graph 1500. In one aspect, the MST guarantees a unique path from each node (het) to any other node (het). The optimal tree 1550 can then be used to determine the two likely haplotypes based on the sequencing information.

Figure 15C:
FIG. 15C shows the haplotypes determined from optimal tree 1550 according to embodiments of the present invention.

FIG. 15C shows the haplotypes determined from optimal tree 1550 according to embodiments of the present invention. Upon application of methods described above (e.g., steps 970 and/or 1270), each het can stay in its original position or be flipped based on an aggregate orientation relative to the anchor het 1510. For example, final het 1570 is flipped. The first haplotype is determined to be C, C, G, C, A, G. The second haplotype is determined to be G, A, T, T, T, A. If the second candidate het, which has not connections, is included as a wildcard (or don't care), then the two haplotypes can be written as C-CGCAG and G-ATTTA.

VI. Universal Phasing

In some embodiments, it is possible that all of the hets of a chromosome are sufficiently connected to form a single graph, and thus potentially can define one contiguous section (contig) that spans the entire chromosome. However, such level of interconnectivity can be rare, and/or result only from extensive sequencing information, which can increase costs considerably. Thus, there usually are many contigs on a single chromosome, where the haplotypes of each contig can be calculated as above. Accordingly, some embodiments match the haplotypes of the various contigs in order to reconstruct the entire copies of the chromosome.

FIG. 16A shows graphs of two separated contigs according to embodiments of the present invention. As mentioned above, the connection information about hets on a chromosome may provide two sets (e.g., graphs) of hets that are not connected. In the example shown, graph 1610 shows a first set of hets and the connections among certain pairs of hets in the set. Another graph 1620 shows a second set of hets and the connections among certain pairs of hets in the set.

As one can see, none of the hets of graph 1610 connect with any hets of graph 1620. Such a separation can be a complete break such that het 1612 and any hets behind it do not have a connection to a het in front of it. As another example, graph 1610 could include hets that are to the right of het 1622 of graph 1620. For instance, assume that het 1652 is not connected to any het of graph 1620, but instead is connected to het 1612. Similarly, het 1622 of graph 1620 could be connected to a het to the left of het 1612 of graph 1610. Breaks in connectivity can be because the DNA is fragmented, a low density of hets, a poly-N sequence on the reference genome, and DNA repeat regions (which can be prone to mismapping). In one embodiment, one can encounter about 100-500 contigs for a chromosome.

FIG. 16B shows an example of connection information having a low strength in a region between the final and beginning hets to two separate graphs according to embodiments of the present invention. In some embodiments, criteria can be used to identify different contigs. For example, if the connection information between het 1612 of graph 1610 does show some level of connection to het 1622 of graph 1620, the level of connection can be small enough that a connection is dropped, effectively providing a determination that no connection exists. One can reduce the number of contigs, by being aggressive in accepting connections, but this can cause errors.

In one implementation, two graphs are required to have more than one connection or otherwise the one connection is dropped, and two contigs are created. For example, if there is only one connection between each contig, then there is little redundant information that can help identify conflicts or other errors; and therefore, accuracy could be lost. In another implementation, a strength of a connection between the two graphs could be compared to a threshold, and if the strength is below the threshold, the two graphs may not be joined (i.e. kept as separate contigs). This threshold can be the same or different than the threshold used to determine whether any connection is strong enough to be part of a any graph, as is mentioned above. For example, if only one connection exists between the graphs, the connection may be kept if its strength is quite high (e.g., greater than 0.7). In one embodiment, a single graph could be broken into multiple graphs based on a resulting optimal tree. For example, the optimal tree could have a connection with a very low strength, and the graph could be broken at a point associated with that week connection.

As shown, one het 1630 does exist between the two contigs, and het 1630 is connected to each graph via one connection. However, the connection to het 1612 has strength of only 0.3, and the connection to het 1622 has a strength of only 0.2. Now, although each graph does show connection with strengths this low, a more stringent threshold can be applied since there is only one connection. Other criteria can also be applied since the connection between hets 1612 and 1614 is through het 1630, which is not connected to any other het. Such criteria can keep accurate connection information of a dense graph to the left and a dense graph to the right, with only one connection between, by dropping the connection between the graphs.

Accordingly, one can know the different haplotypes of contigs (e.g. those corresponding to graphs 1610 and 1620), but not know the phasing between the contigs. That is one can determine the two haplotypes corresponding to graph 1610 and the two haplotypes corresponding to graph 1620. But, one does not know which haplotype of graph 1610 is on the same chromosome as a first haplotype of graph 1620.

As mentioned above, the connection information can be redundant in that two edges can cover the same part of a graph. For example, het 1622 and het 1652 do not have an edge (connection) displayed, e.g., due to the sequencing information not containing sufficient connection information between these two hets. However, connections 1650 and 1654 do provide connection information to the right side of het 1622, thereby allowing het 1622 to be part of graph 1620 and to effectively provide the connection information between het 1622 and het 1652. In one embodiment, more than 10% or 30% of the possible first neighbor connections (i.e. between hets right next to each other) are found not to exist in the sequencing information (e.g., if the 2-allele haplotypes of a particular orientation are not sufficiently linked, which may occur when the strength is below a significance threshold).

Figure 17:
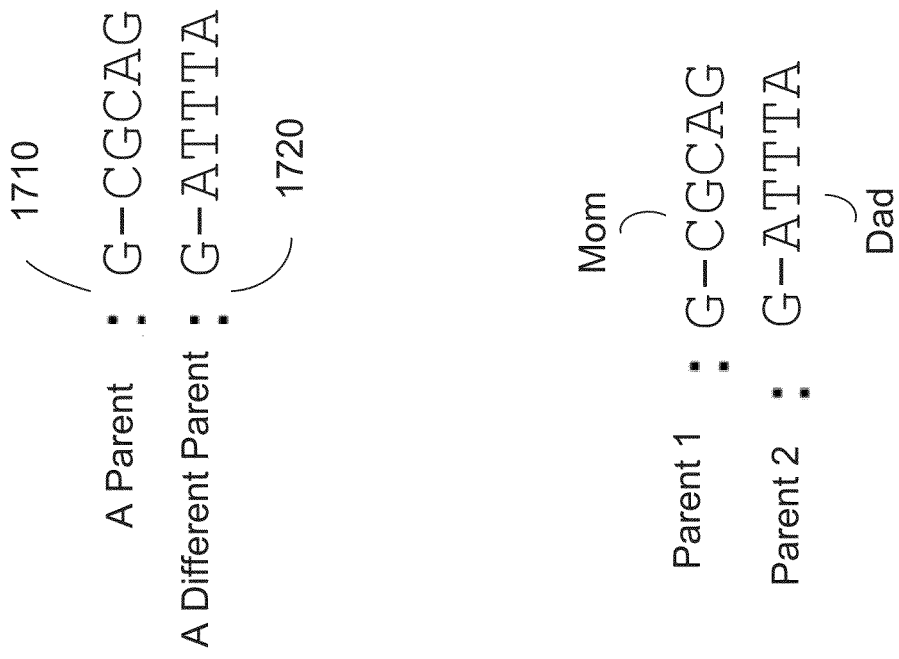
FIG. 17 highlights contig phasing and universal phasing according to embodiments of the present invention.

FIG. 17 highlights contig phasing and universal phasing according to embodiments of the present invention. The contig phasing can determine one haplotype 1710 and another haplotype 1720, e.g., by methods described herein. However, at best one known that haplotype 1710 is from a first parent and haplotype 1720 is from a different parent, but we do not know which parent. And, we cannot state whether haplotype of another contig corresponds to the same parent as haplotype 1710. Thus, in one embodiment, after the contigs are phased to determine the haplotypes of each contig, each of the contigs are phased.

For universal phasing, the haplotypes are associated with a particular parent. In one embodiment, this could simply be a designation of parent 1 and parent 2. Such a designation could be determined using some level of connection information. For example, it may be advantageous to determine haplotypes of contigs from relatively dense graphs, and then later phase the contigs by using connections between hets of different contigs. Such a hierarchal approach to phasing can be repeated across many levels. Thus, one can determine haplotypes for short graphs (e.g. short dense graphs), and then combine the short graphs into larger graphs just using the connections between the short graphs, and so on.

In one implementation, the length of the fragments can be varied, and thus connections between pairs of hets of various spacing between the hets can be obtained. Thus, some connections might span across contigs. For example, shorter fragments can be used to determine the contigs, and longer fragments can be used to connect the contigs. In one aspect, such a technique may be more appropriate when using mate pairs to determine connection information. Such embodiments effectively can determine a copy of chromosome as a single contig. In another implementation, sequencing information from a population can be used. For example, if the population shows a connection between two hets, which happen to be on different contigs, then that information can be used to identify the two contigs as being on a same chromosome.

In other embodiments, no connection information is known and thus other techniques can be used, as is described below. For example, one can use genomic information of the parents of the person whose genome is being mapped to match a haplotype of a particular contig to a specific parent. In one embodiment, this information can be obtained by doing a Trio (Mom-Dad-Child) phasing. In another embodiment, the information can be obtained from just one parent. In one implementation, the parental information can be just genotyping information, e.g., using a SNP chip.

Figure 18:
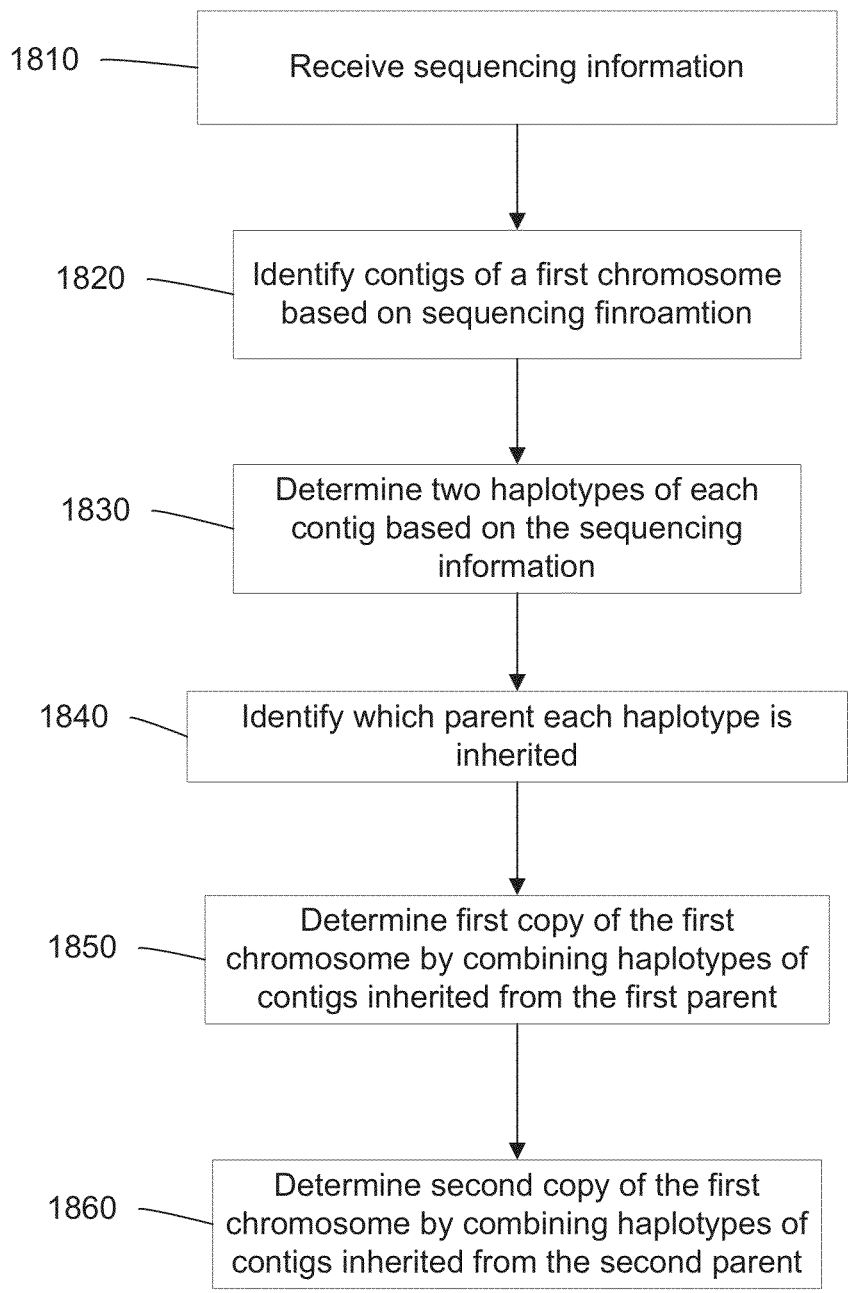
FIG. 18 is a flowchart illustrating a method 1800 of determining a sequence of a chromosome of a first organism from one or more samples.

FIG. 18 is a flowchart illustrating a method 1800 of determining a sequence of a chromosome of a first organism from one or more samples. The one or more samples include nucleic acid molecules of the first organism. The first organism has a first parent and a second parent. Various steps of method 1800 correspond to embodiments for performing step 140 of method 100.

In step 1810, sequencing information of a plurality of the nucleic acid molecules in the one or more samples is received. The sequencing information can have many forms, e.g., as is described herein.

In step 1820, a plurality of contiguous sections of the genome of a first chromosome are identified based on the sequencing data. In one embodiment, each of the plurality of contiguous sections do not overlap with another of the plurality of contiguous sections. Note that other overlapping contigs could be used in addition to the plurality of non-overlapping contigs. In one embodiment, the contiguous sections (contigs) can be determined by identifying connections between hets and then determining graphs of connections. Two separate graphs can correspond to separated contigs. As mentioned above, two graphs may be separated when there is no or insufficient connection information between them, or potentially just connection information that is less dense between the graphs than within a graph. For example, steps of methods 400, 900, and/or 1200 may be used to determine contigs. In other embodiments, other methods may be used, as would be apparent to one skilled in the art.

Figure 19A:
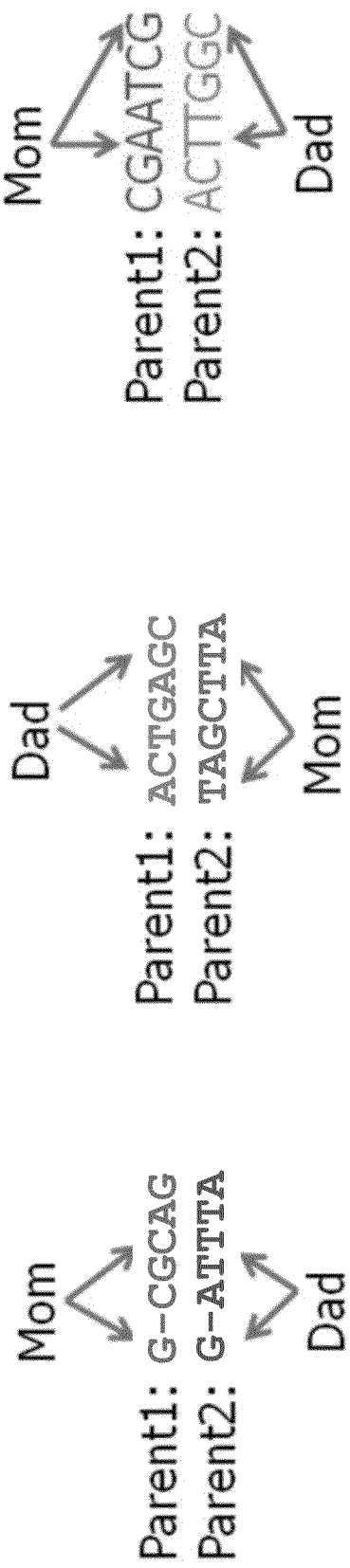
FIG. 19A shows an example of the haplotypes for three contigs.

In step 1830, two haplotypes are determined for each contiguous section of the first chromosome based on the sequencing information. For example, methods 400, 900, or 1200 can be used to determine the two haplotypes. Other embodiments for determining the haplotypes include clustering mate pair reads of a same fragment that aligns to the contiguous section. FIG. 19A shows an example of the haplotypes for three contigs. Note that the designation of parent 1 or parent 2 is arbitrary, and just distinguishes the two haplotypes of one contig.

Figure 19B:
FIG. 19B shows the haplotype associated with the mom for each contig, and below that is shown the haplotype associated with the dad for each contig.

In step 1840, the parent from which each haplotype is inherited is identified. In one embodiment, the parent corresponding to a particular haplotype of a particular contig is determined based on other sequencing information of one or more second organisms that are related to the first organism. For example, genomic information from the parents could be used. In FIG. 19A, each haplotype is shown identified as being from the mom or Dad. FIG. 19B shows the haplotype associated with the mom for each contig, and below that is shown the haplotype associated with the dad for each contig.

In one implementation, the genotype of each parent can be determined at a particular locus within a first contig. The locus corresponds to a het in the first contig. For example, assume that the mother is homozygous AA at the locus, the father is AC, and the person being tested is AC at that locus. Then one can determine that the haplotype with C corresponds to the father. The other haplotype is thus associated with the mother. Similarly, a locus can be identified as having an allele that is specific to the mother. Thus, one can determine which parent each contig is from. Multiple loci can be used for a particular contig to obtain more accurate results, or confirm results.

Figure 19C:
FIG. 19C shows the three haplotypes corresponding to the mom combined, and the three haplotypes corresponding to the dad combined.

In step 1850, at least a portion of a first copy of the first chromosome is determined by combining the haplotypes of the plurality of sections that are inherited from the first parent. In step 1860, at least a portion of a second copy of the first chromosome is determined by combining the haplotypes of the plurality of sections that are inherited from the second parent. FIG. 19C shows the three haplotypes corresponding to the mom combined, and the three haplotypes corresponding to the dad combined. Note that the sequences between the hets can be taken as that of the reference genome or from a parent, if that was known.

The parental information can also be used to identify errors within a contig. For example, this could occur when a wrong orientation was chosen for a particular connection (thus a flip occurred when it should not have). After combining the haplotypes, the resulting sequence of the chromosome might still have gaps corresponding to the area between the contigs, but such areas can be filled in based on reads, e.g., that show the loci in the gap to be homozygous, which may equal the reference genome. In one aspect, gaps are only filled in if evidence (e.g., sequencing information and/or the reference) shows that the locations in the gap are deemed to be homozygous with sufficient confidence.

FIG. 20 shows an illustration of showing a process of universal phasing for a reference genome 2010 according to embodiments of the present invention. In reference genome 2010, hets are shown at particular highlighted locations. A collection of three contigs 2020 shows determined haplotypes for each contig. The contigs are displayed respective positions so that the loci of the haplotypes are at a same height as in the reference genome 2010. Each haplotype is shown with different shading as the origin (parent) of each haplotype is not known. As one can see, a contig can include alleles outside of a het. For example, contig 2021 has an allele A at a locus 2022 that is outside of the het A/C. Thus, a contig can include loci not between the first and last het. This can occur, for example, since sequencing information may be known, and the loci are homozygous.

After universal phasing, the contigs 2030 show matching haplotypes with a same shading. For example, haplotypes 2031, 2032, and 2033 are from the same parent. The haplotypes can then be combined to from the two sequences 2040. As shown, haplotypes 2031, 2032, and 2033 are combined onto the same chromosome copy. Note that the loci 2041 and 2042 were not part of the contigs 2020, but their value was obtained from reference genome 2010. In another implementation, the sequence information from a parent can be used to fill in the gaps.

An experiment was performed for a particular sample, where genomes of the Mom and Dad were also obtained. Using the trio's sequenced genomes, we identified some loci with known parental associations. These associations were then used to assign the correct parental label (Mom/Dad) on the contigs. For high accuracy, we did the following: 1) acquired the trio information from multiple sources, and used a combination of them; 2) required the contigs to have at least 2 known trio-phased loci on them; 3) eliminated the contigs that had a series of trio-mismatches in-a-row on them (indicating a segmental error); and 4) eliminated the contigs that had a single trio-mismatch at the end of the trio loci (indicating a potential segmental error).

As an example, statistics for an experiment of phasing a whole genome are now listed. (1) A total candidate hets fed into the system was 3.7 M. (2) A total estimated number of hets was 2.8-2.9 M. (3) A total number of phased contigs was 12,705. (4) A total number of connected hets (and phased) as determined from LFR data was 2.38 M. (5) A total number of trio-guided LFR phased hets was 2.31 M. (6) A total number of Trio phased was 1.74 M. (7) The union of hets in (5) and (6) was 2.59 M. A number of discordant hets (Trio vs. Trio-guided-LFR) was 81 (<0.005%). In one aspect, a discordant het is when the sequencing information from a sample suggests one phase (e.g., for C/T het, C from Mom and T from Dad), while the trio phasing suggests the opposite phase. Such a discordant het can be the result of an error in the sequencing information or the trio phasing, or an analysis of any data.

Another validation is for chromosome X. The child's X was phased to get child's X from Mom (cXm) and child's X from Dad (cXd). Dad's X Chromosome (Xd) was sequenced. Then we compared Xd to cXd in the non-pseudo-autosomal regions by looking into the calls that are: Het or Homo in the cXd, Homo in Xd, and Homo in cXd. We then counted the number of discordances between Xd and cXd. The number of errors was 0 out of 20618.

VII. Examples for Connectivity Matrices

A. Confirming Hets

As mentioned above the strength can be used to confirm the existence of a het and the connection. An advantage of the connectivity matrices and/or LFR sequencing information is an increase of the accuracy of the het calling. Below, there are two examples of such correction. FIG. 21A shows a connectivity matrix that does not support any of the expected hypotheses. This is can be indication that one of the hets is not really a het. In this example, the A/C het is in reality a homozygous locus (A/A), which was mislabeled as a heterozygous locus by the assembler. This error can be identified, and either eliminated or (in this case) corrected. FIG. 21B shows a connectivity matrix that supports both hypotheses at the same time. This is a sign that the heterozygous calls are not real. In one embodiment, a "healthy" het-connection matrix is one that has only two high cells (at the expected het positions). In one aspect, all other possibilities can point to potential problems, and can be eliminated.

Another advantage is an ability to call hets with weak supports (e.g., where it was hard to map DNBs due to a bias or mismatch rate). Since the LFR process requires an extra constraint (e.g. reads being from a same aliquot) on the hets, one could reduce the threshold that a het call requires in a non-LFR assembler. FIGS. 21C and 21D demonstrate an example of this case. In FIG. 21D, under a normal scenario, the low number of supporting reads would have prevented any assembler to confidently call the corresponding hets. However, since the connectivity matrix is "clean" (low impurity), one could more confidently assign het calls to these loci. A confident het call could be made despite a small number of reads. Thus, using an impurity concept, false negatives can be decreased.

B. Calculating Strength Score

In one embodiment, the values of the connectivity matrix can be input into fuzzy inference engine (which may be another system or included within other systems described herein) to determine the score. For example, the logic can be If-Then statements, which determine a truth of a particular hypothesis, with one being true and 0.5 being exactly half-true (in a sense a probability that it is true). In one embodiment, the variables (e.g. those from the matrix elements from the connectivity matrix) are used as inputs to one or more functions. The output values of the functions can then be input into other logic, e.g., If Then logic.

In one implementation, the rules of the fuzzy inference engine are in the following order, where the first one that is satisfied is taken. Note that small, medium, large, and very large can be pre-defined ranges or particular values. (1) If Energy1 is small and Energy2 is small, then the score is very small. (2) If Energy1 is medium and Energy2 is small, then Score is small. (3) If Energy1 is medium and Energy2 is medium, then the score is medium. (4) If Energy1 is large and Energy2 is small, then Score is medium. (5) If Energy1 is large and Energy2 is medium, then the score is large. (6) If Energy1 is large and Energy2 is large, then the score is very large. (7) If Impurity is small, then the score is large. (8) If Impurity is medium, then the score is small. (9) If Impurity is large, then the score is very small. In one aspect, for each variable, the definition of small, medium and large can be different, and can be governed by its specific membership functions.

Figure 22:
FIG. 22 shows the memberships for each variable (in the vertical direction) according to embodiments of the present invention.

FIG. 22 shows the memberships for each variable (in the vertical direction) according to embodiments of the present invention. After exposing the fuzzy inference engine to each variable set, the contribution of the input set on the rules are propagated through the fuzzy inference engine, and a single (de-fuzzified) number (the strength score) is generated at the output. In this example, the score is limited between 0 and 1, with 1 showing the best possible quality. FIG. 22 demonstrates the incorporation of the fuzzy rules, and the defuzzification process in the output.

FIG. 23 shows output curves for determining strength values according to embodiments of the present invention. In this example, different three dimensional curves are used to determine the strength. Each curve is for a fixed impurity value. The two curves are for fixed impurity values of 0 and 0.5. As one can see, the curve with the lower impurity corresponds to higher strength scores. In other embodiments, machine learning, such as supervised learning (e.g., neural networks), unsupervised learning, semi-supervised learning, and reinforcement learning, or other methods can be used to determine the score.

C. Correcting Base Calls Between Hets

In the example above for FIGS. 15A-15C, the two haplotypes for the contig defined of graph 1500 were C-CGCAG and G-ATTTA. The second candidate het 1520 of FIG. 15B was initially identified as a candidate het, e.g., because different alleles were detected at the loci. However, none of the other hets had connections to candidate het 1520. For example, the connectivity matrices involving loci 1520 may have had weak strengths, and thus were not strong enough to be considered connections. Thus, candidate het 1520 ultimately was not included in the phasing.

However, after phasing, one embodiment can investigate such loci and other loci with the added information of knowing the haplotypes. Such investigation can correct errors, or fill in missing information. Examples of loci that can be investigated include: (1) heterozygous loci, which can be signified as A/B (such as candidate "weak" hets whose strength was below a threshold); (2) homozygous loci, which can be signified as BB or just B; (3) half-called loci, which can be signified as B/N; and (4) Uncalled or nocalled loci, which can be signified as N/N. With the investigation, some embodiments can determine with greater accuracy whether a loci is indeed a het, is actually homozygous, and resolve nocalls.

For example, for a heterozygous locus, it could be verified if this locus is a true het, and if it is, what the phasing for its alleles are. This can include a case where only one of the two alleles is consistent with the haplotype (contig) phasing. The result of the investigation can also be a nocall in one of both alleles of the loci, which in effect can be considered a correction of an error of the initial call, since the confidence of the call is not sufficient. Thus, a resolution can be A/N, B/N, N/N or A/B.

For a homozygous locus, it could be verified if the B call is supported by zero, one, or two haplotypes. The resolution can be a confirmation of the B/B homozygosity, or include a nocall (N/N, B/N), for example, if the sequencing information shows a lack of information for one of the haplotypes, and even could also result in a het call of A/B. For a half-called locus, the state of the known and the unknown base can be verified/validated. Again, the resolution could be B/N, N/N, A/B, or B/B. For an uncalled locus, the state of one or both alleles also can be resolved with the results also being N/N, B/N, A/B or B/B.

Embodiments can investigate these other loci (i.e. loci that were not used as hets to determine the haplotypes of a contig) in various ways. One embodiment uses connectivity matrices, which are described above. In one embodiment, for the locus of interest and an adjacent loci (which must be a part of the phased contigs), a 4×4 connectivity matrix is constructed, e.g., like matrix 730 of FIG. 7B. A matrix can be constructed for each of multiple adjacent loci, including direct neighbors and loci that are further away.

For instance, if there are two strong cells, and the location of these cells are consistent with the calls, the associated calls can be considered validated, and can be reflected in the state of phasing. For example, consider the following scenario. The call for the locus of interest is A, and the next locus (part of the phased contig) is C/G. FIG. 24A shows a connectivity matrix 2400 corresponding to this example. For the above conditions, one can infer that the actual call is A/A since A is connected to C on one haplotype (evidenced by 9), and on the other A is connected to a G on the other haplotype (evidenced by 12). Therefore, not only has the state of A/A been validated, this validation has been done on both haplotypes.

On the other hand, the connectivity matrix 2430 of FIG. 24B shows an example where A/A is not validated. Instead of "12", the matrix element for (A,G) is "1". Thus, what might have initially been considered an A/A (e.g., since most of the reads showed an A), is actually an A/N. Thus, we know that there is an A on the same haplotype that the C allele is on; however, there is no evidence for another A on the haplotype that includes the G allele. Embodiments can use the techniques of calculating a strength for a particular hypothesis (e.g., as described above for connections among hets) for any of these other types of loci. The strength can be compared to a threshold to distinguish a call from a no call. For example, if the matrix element for (A,G) was "3" and with the impurity of "2", a strength score could be determined for the hypothesis that the second haplotype is indeed (A,G) or is a nocall that would give (A,N)

FIG. 24C shows a connectivity matrix 2450 as an example of recovering from a half-call. Suppose the call is A/N, and the following locus has been C/G (like the above example). Since the matrix element for (A,G) is "3", one may conclude that the actual call should be A/A, with N being converted to A. In addition to that, the exact phasing of A alleles on both haplotypes has also been resolved (similar to the above example).

VIII. Computer System

Any of the methods described herein may be totally or partially performed with a computer system including a processor, which can be configured to perform the steps. Thus, embodiments can be directed to computer systems configured to perform the steps of any of the methods described herein, potentially with different components performing a respective steps or a respective group of steps. Although presented as numbered steps, steps of methods herein can be performed at a same time or in a different order. Additionally, portions of these steps may be used with portions of other steps from other methods. Also, all or portions of a step may be optional. Additionally, any of the steps of any of the methods can be performed with modules, circuits, or other means for performing these steps.

Figure 25:
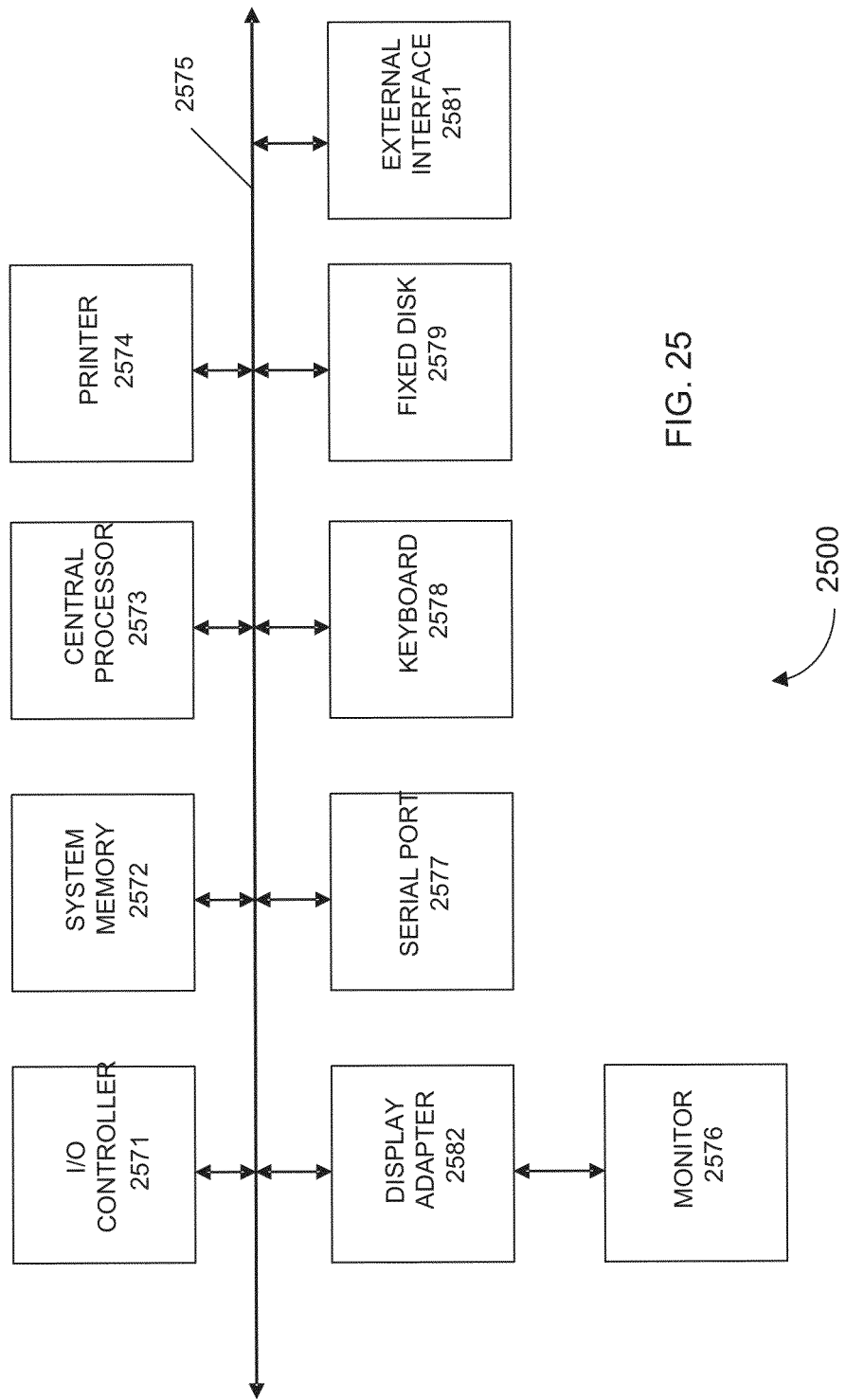
FIG. 25 shows a block diagram of an example computer system 2500 usable with system and methods according to embodiments of the present invention.

Any of the computer systems mentioned herein may utilize any suitable number of subsystems. Examples of such subsystems are shown in FIG. 25 in computer apparatus 2500. In some embodiments, a computer system includes a single computer apparatus, where the subsystems can be the components of the computer apparatus. In other embodiments, a computer system can include multiple computer apparatuses, each being a subsystem, with internal components.

The subsystems shown in FIG. 25 are interconnected via a system bus 2575. Additional subsystems such as a printer 2574, keyboard 2578, fixed disk 2579, monitor 2576, which is coupled to display adapter 2582, and others are shown. Peripherals and input/output (I/O) devices, which couple to I/O controller 2571, can be connected to the computer system by any number of means known in the art, such as serial port 2577. For example, serial port 2577 or external interface 2581 can be used to connect computer system 2500 to a wide area network such as the Internet, a mouse input device, or a scanner. External interface 2581 is an example of an input that can receive sequencing information. The interconnection via system bus 2575 allows the central processor 2573 to communicate with each subsystem and to control the execution of instructions from system memory 2572 or the fixed disk 2579, as well as the exchange of information between subsystems. The system memory 2572 and/or the fixed disk 2579 may embody a computer readable medium. Any of the values mentioned herein can be output from one component to another component and can be output to the user.

A computer system can include a plurality of the same components or subsystems, e.g., connected together by external interface 2581 or by an internal interface. In some embodiments, computer systems, subsystem, or apparatuses can communicate over a network. In such instances, one computer can be considered a client and another computer a server, where each can be part of a same computer system. A client and a server can each include multiple systems, subsystems, or components.

It should be understood that any of the embodiments of the present invention can be implemented in the form of control logic using hardware and/or using computer software in a modular or integrated manner. Based on the disclosure and teachings provided herein, a person of ordinary skill in the art will know and appreciate other ways and/or methods to implement embodiments of the present invention using hardware and a combination of hardware and software.

Any of the software components or functions described in this application may be implemented as software code to be executed by a processor using any suitable computer language such as, for example, Java, C++ or Perl using, for example, conventional or object-oriented techniques. The software code may be stored as a series of instructions or commands on a computer readable medium for storage and/or transmission, suitable media include random access memory (RAM), a read only memory (ROM), a magnetic medium such as a hard-drive or a floppy disk, or an optical medium such as a compact disk (CD) or DVD (digital versatile disk), flash memory, and the like. The computer readable medium may be any combination of such storage or transmission devices.

Such programs may also be encoded and transmitted using carrier signals adapted for transmission via wired, optical, and/or wireless networks conforming to a variety of protocols, including the Internet. As such, a computer readable medium according to an embodiment of the present invention may be created using a data signal encoded with such programs. Computer readable media encoded with the program code may be packaged with a compatible device or provided separately from other devices (e.g., via Internet download). Any such computer readable medium may reside on or within a single computer program product (e.g. a hard drive, a CD, or an entire computer system), and may be present on or within different computer program products within a system or network. A computer system may include a monitor, printer, or other suitable display for providing any of the results mentioned herein to a user.

The specific details of particular embodiments may be combined in any suitable manner without departing from the spirit and scope of embodiments of the invention. However, other embodiments of the invention may be directed to specific embodiments relating to each individual aspect, or specific combinations of these individual aspects.

The above description of exemplary embodiments of the invention has been presented for the purposes of illustration and description. It is not intended to be exhaustive or to limit the invention to the precise form described, and many modifications and variations are possible in light of the teaching above. The embodiments were chosen and described in order to best explain the principles of the invention and its practical applications to thereby enable others skilled in the art to best utilize the invention in various embodiments and with various modifications as are suited to the particular use contemplated.

A recitation of "a", "an" or "the" is intended to mean "one or more" unless specifically indicated to the contrary.

All patents, patent applications, publications, and descriptions mentioned above are herein incorporated by reference in their entirety for all purposes. None is admitted to be prior art.

What is claimed is:

1. A method of determining at least part of a genome of an organism from one or more samples, the one or more samples including nucleic acid molecules of the organism, the method comprising:
receiving sequencing information of a plurality of the nucleic acid molecules in the one or more samples;
identifying a plurality of loci of a first chromosome;
computing, with a computer system, a first strength conveying a likelihood that a first allele of a first locus and a second allele of a second locus are on a first 2-allele haplotype of the organism, wherein computing the first strength includes:
determining a first positive contribution to the likelihood based on sequencing information consistent with the first allele and the second allele being on the first 2-allele haplotype;
determining a first negative contribution to the likelihood based on sequencing information inconsistent with the first allele and the second allele being on the first 2-allele haplotype; and
using the first positive and first negative contributions to compute the first strength; and
calculating two haplotypes involving the first locus and the second locus using the first strength.

2. The method of claim 1, wherein using the first positive and first negative contributions to compute the first strength includes inputting the first positive and first negative contributions into a fuzzy logic engine that outputs the first strength.

3. The method of claim 1, wherein calculating two haplotypes involving the first locus and the second locus using the first strength includes confirming and/or correcting a base call at at least one of the first and second locus.

4. The method of claim 3, wherein confirming and/or correcting a base call at at least one of the first and second locus includes determining a nocall to be at one of the first or second loci for one of the two haplotypes.

5. The method of claim 1, wherein determining the first positive contribution includes identifying a number of reads that are correlated and that have the first allele at the first locus and the second allele at the second locus.

6. The method of claim 5, further comprising:
scaling each of the number of reads by a factor that is dependent on a type of correlation for the respective read.

7. The method of claim 6, wherein the types of correlations include at least two of: two alleles being on a same read, two alleles being on mated pair reads, and two alleles being from a same aliquot of a sample of the organism.

8. The method of claim 1, wherein the two haplotypes are of size N-allele haplotypes, wherein N is greater than two.

9. The method of claim 1, wherein the second locus is a heterozygous loci that has been used to phase haplotypes involving the second locus, and wherein calculating two haplotypes involving the first locus and the second locus using the first strength includes:
using the phased haplotypes and the first strength to calculate whether the first allele of the first locus is on a particular phased haplotype.

10. The method of claim 9, wherein the first locus is not a heterozygous locus.

11. The method of claim 10, wherein non-heterozygous loci include homozygous loci and loci that include a nocall for a base.

12. The method of claim 10, further comprising:
computing a plurality of additional strengths, each conveying a likelihood that the first allele of the first locus and a second allele of an additional locus are on a 2-allele haplotype of the organism, wherein each additional locus is a heterozygous loci that has been used to phase haplotypes.

13. The method of claim 1, wherein the plurality of loci include a plurality of candidate hets, a candidate het being a locus identified as having or potentially having two or more different alleles, and wherein the first locus is a first candidate het and the second locus is a second candidate het.

14. The method of claim 13, further comprising:
computing one or more additional strengths, each conveying a likelihood that the first allele of the first candidate het and a second allele of an additional candidate are on a 2-allele haplotype of the organism.

15. The method of claim 13, wherein the first strength also conveys a likelihood that a third allele of the first candidate het and a fourth allele of the second candidate het are on a second 2-allele haplotype of the organism.

16. The method of claim 15, wherein determining the first positive contribution to the likelihood is also based on sequencing information consistent with the third allele and the fourth allele being on the second 2-allele haplotype, and wherein determining the first negative contribution to the likelihood is also based on sequencing information inconsistent with the third allele and the fourth allele being on the second 2-allele haplotype.

17. The method of claim 13, wherein the first strength also conveys a likelihood that a third allele of the first candidate het and a fourth allele of the fourth candidate het are on a second 2-allele haplotype of the organism, wherein computing the first strength includes:
 determining a second positive contribution to the likelihood based on sequencing information consistent with the third allele and the fourth allele being on the second 2-allele haplotype,
 wherein determining the first negative contribution to the likelihood is also based on sequencing information inconsistent with the third allele and the fourth allele being on the second 2-allele haplotype; and
 using the first positive contribution, the second positive contribution, and the first negative contribution to compute the first strength.

18. The method of claim 17, further comprising:
 computing a second strength conveying a likelihood that the first allele of the first candidate het and the fourth allele of the second candidate het are on the first 2-allele haplotype and that the third allele of the first candidate het and the second allele of the second candidate het are on the second 2-allele haplotype, wherein computing the first strength includes:
  determining a third positive contribution to the likelihood based on sequencing information consistent with the first allele and the fourth allele being on the first 2-allele haplotype;
  determining a fourth positive contribution to the likelihood based on sequencing information consistent with the third allele and the second allele being on the second 2-allele haplotype;
  determining a second negative contribution to the likelihood based on sequencing information inconsistent with the first allele and the fourth allele being on the first 2-allele haplotype and with the third allele and the second allele being on the second 2-allele haplotype; and
  using the third positive contribution, the fourth positive contribution, and the second negative contribution to compute the second strength; and
 calculating the two haplotypes involving the first candidate het and the second candidate het using the first strength and the second strength.

19. The method of claim 18, wherein calculating the two haplotypes involving the first candidate het and the second candidate het using the first strength and the second strength includes:
 comparing the first strength and the second strength;
 selecting an optimal strength based on the comparison; and
 determining the first and second 2-allele haplotypes as having the alleles corresponding to the optimal strength.

20. The method of claim 19, wherein the strength with the higher value is selected as the optimal strength.

21. The method of claim 1, wherein the organism has two parents, the method further comprising:
 calculating two haplotypes for a plurality of regions of the first chromosome based on the sequencing information;
 obtaining genomic information about the parents;
 for each region:
  determining a heterozygous locus of the organism where the genomic information about the parents indicates a particular allele at the heterozygous locus is from a particular parent;
  associating each haplotype of the region with a respective parent based on the particular allele at the heterozygous locus being from a particular parent;
 combining the haplotypes associated with the first parent on a first copy of the chromosome; and
 combining the haplotypes associated with the second parent on a second copy of the chromosome.

22. The method of claim 21, wherein obtaining genomic information about the parents includes obtaining genotyping information for over 100,000 loci for at least one parent.

23. The method of claim 21, wherein obtaining genomic information about the parents includes obtaining genotyping information for over 300,000 loci for at least one parent.

24. The method of claim 21, wherein obtaining genomic information about the parents includes obtaining genotyping information for over one million loci for at least one parent.

25. A computer program product comprising a tangible computer readable medium storing a plurality of instructions for controlling a processor to perform an operation for determining at least part of a genome of an organism from one or more samples, the one or more samples including nucleic acid molecules of the organism, the instructions comprising:
 receiving sequencing information of a plurality of the nucleic acid molecules in the one or more samples;
 identifying a plurality of loci of a first chromosome;
 computing a first strength conveying a likelihood that a first allele of a first locus and a second allele of a second locus are on a first 2-allele haplotype of the organism, wherein computing the first strength includes:
  determining a first positive contribution to the likelihood based on sequencing information consistent with the first allele and the second allele being on the first 2-allele haplotype;
  determining a first negative contribution to the likelihood based on sequencing information inconsistent with the first allele and the second allele being on the first 2-allele haplotype; and
  using the first positive and first negative contributions to compute the first strength; and
 calculating two haplotypes involving the first locus and the second locus using the first strength.

26. A system for determining at least part of a genome of an organism from one or more samples, the one or more samples including nucleic acid molecules of the organism, the system comprising:
 an input for receiving sequencing information of a plurality of the nucleic acid molecules in the one or more samples; and
 one or more processors configured to:
  identify a plurality of loci of a first chromosome;
  compute a first strength conveying a likelihood that a first allele of a first locus and a second allele of a second locus are on a first 2-allele haplotype of the organism, wherein computing the first strength includes:
   determining a first positive contribution to the likelihood based on sequencing information consistent with the first allele and the second allele being on the first 2-allele haplotype;

determining a first negative contribution to the likelihood based on sequencing information inconsistent with the first allele and the second allele being on the first 2-allele haplotype; and using the first positive and first negative contributions to compute the first strength; and calculate two haplotypes involving the first locus and the second locus using the first strength.

* * * * *

```
SEQUENCE LISTING

<160> NUMBER OF SEQ ID NOS: 4

<210> SEQ ID NO 1
<211> LENGTH: 19
<212> TYPE: DNA
<213> ORGANISM: Artificial Sequence
<220> FEATURE:
<223> OTHER INFORMATION: synthetic reference genome 2010

<400> SEQUENCE: 1
aatgactaca cattcgcag                                                19

<210> SEQ ID NO 2
<211> LENGTH: 19
<212> TYPE: DNA
<213> ORGANISM: Artificial Sequence
<220> FEATURE:
<223> OTHER INFORMATION: synthetic reference genome 2010

<400> SEQUENCE: 2
actggcttca cctttggat                                                19
```

```
<210> SEQ ID NO 3
<211> LENGTH: 19
<212> TYPE: DNA
<213> ORGANISM: Artificial Sequence
<220> FEATURE:
<223> OTHER INFORMATION: synthetic haplotypes 2040 combined from contig
      sequences 2030 with loci values 2041 and 2042
      obtained from reference genome 2010

<400> SEQUENCE: 3
actgacttca catttggag                                               19

<210> SEQ ID NO 4
<211> LENGTH: 19
<212> TYPE: DNA
<213> ORGANISM: Artificial Sequence
<220> FEATURE:
<223> OTHER INFORMATION: synthetic haplotypes 2040 combined from contig
      sequences 2030 with loci values 2041 and 2042
      obtained from reference genome 2010

<400> SEQUENCE: 4
aatggctaca ccttcgcat                                               19
```